(12) United States Patent
Kalina, Jr.

(10) Patent No.: US 12,226,308 B2
(45) Date of Patent: Feb. 18, 2025

(54) METHOD FOR CONTROLLING PLACEMENT OF INTRAOCULAR IMPLANTS

(71) Applicant: Glaukos Corporation, San Clemente, CA (US)

(72) Inventor: Charles Raymond Kalina, Jr., Irvine, CA (US)

(73) Assignee: Glaukos Corporation, Aliso Viejo, CA (US)

( * ) Notice: Subject to any disclaimer, the term of this patent is extended or adjusted under 35 U.S.C. 154(b) by 861 days.

(21) Appl. No.: 17/444,960

(22) Filed: Aug. 12, 2021

(65) Prior Publication Data
US 2021/0369447 A1 Dec. 2, 2021

Related U.S. Application Data

(62) Division of application No. 16/146,786, filed on Sep. 28, 2018, now Pat. No. 11,116,625.
(Continued)

(51) Int. Cl.
*A61M 1/00* (2006.01)
*A61B 5/026* (2006.01)
(Continued)

(52) U.S. Cl.
CPC .......... *A61F 2/1664* (2013.01); *A61B 5/0261* (2013.01); *A61B 5/0295* (2013.01);
(Continued)

(58) Field of Classification Search
CPC ........ A61M 1/80; A61M 60/35; A61M 60/31; A61M 60/00; A61M 60/405
See application file for complete search history.

(56) References Cited

U.S. PATENT DOCUMENTS

| 2,031,754 A | 2/1936 | Bacigalupi |
| 2,127,903 A | 8/1938 | Bowen |

(Continued)

FOREIGN PATENT DOCUMENTS

| AU | 199876197 | 2/1999 |
| AU | 200072059 | 12/2000 |

(Continued)

OTHER PUBLICATIONS

Alexander, L., et al., Disistronic Polloviruses as Expression Vectors for Foreign Genes. 1994. Aids Research and Human Retroviruses. vol. 10, Supplement 2, S57-S60.
(Continued)

*Primary Examiner* — Leslie R Deak
(74) *Attorney, Agent, or Firm* — Knobbe, Martens, Olson & Bear, LLP

(57) ABSTRACT

Some embodiments disclosed herein relate to devices and methods for controlling placement of intraocular implants within a patient's eye including but not limited to placement within or near the collector ducts of Schlemm's canal located behind the trabecular meshwork. In some embodiments, a handheld peristaltic rotor device having a compression element can be positioned on a corneal surface of the eye and rotated to create a peristaltic movement of blood in one or more episcleral veins to generate blood reflux within Schlemm's canal such that one or more collector ducts, or channels, of Schlemm's canal can be located. In some embodiments, an implant can be implanted near the identified location of the one or more collector ducts, or channels.

10 Claims, 14 Drawing Sheets

Related U.S. Application Data

(60) Provisional application No. 62/564,972, filed on Sep. 28, 2017.

(51) Int. Cl.

| | | |
|---|---|---|
| *A61B 5/0295* | (2006.01) | |
| *A61F 2/16* | (2006.01) | |
| *A61F 9/00* | (2006.01) | |
| *A61M 60/31* | (2021.01) | |
| *A61M 60/35* | (2021.01) | |
| *A61M 60/405* | (2021.01) | |
| *A61B 3/117* | (2006.01) | |
| *A61F 9/007* | (2006.01) | |
| *A61F 9/008* | (2006.01) | |

(52) U.S. Cl.
CPC ............ *A61F 9/0008* (2013.01); *A61M 1/80* (2021.05); *A61M 60/31* (2021.01); *A61M 60/35* (2021.01); *A61M 60/405* (2021.01); *A61B 3/117* (2013.01); *A61F 2009/0052* (2013.01); *A61F 9/00781* (2013.01); *A61F 2009/00872* (2013.01); *A61F 2250/0067* (2013.01)

(56) References Cited

U.S. PATENT DOCUMENTS

| | | | |
|---|---|---|---|
| 2,269,963 A | 1/1942 | Frederick |
| 3,159,161 A | 12/1964 | Ness |
| 3,416,530 A | 12/1968 | Ness |
| 3,439,675 A | 4/1969 | Cohen |
| 3,717,151 A | 2/1973 | Collett |
| 3,788,327 A | 1/1974 | Donowitz et al. |
| 3,827,700 A | 8/1974 | Kaller |
| 3,863,623 A | 2/1975 | Trueblood et al. |
| 3,915,172 A | 10/1975 | Krejci et al. |
| 3,948,271 A | 4/1976 | Akiyama |
| 3,948,871 A | 4/1976 | Butterfield et al. |
| 3,976,077 A | 8/1976 | Kerfoot, Jr. |
| 4,030,480 A | 6/1977 | Meyer |
| 4,037,604 A | 7/1977 | Newkirk |
| 4,043,346 A | 8/1977 | Mobley et al. |
| 4,113,088 A | 9/1978 | Binkhorst |
| 4,168,697 A | 9/1979 | Cantekin |
| 4,175,563 A | 11/1979 | Arenberg et al. |
| 4,299,227 A | 11/1981 | Lincoff |
| 4,366,582 A | 1/1983 | Faulkner |
| 4,402,681 A | 9/1983 | Haas et al. |
| 4,428,746 A | 1/1984 | Mendez |
| 4,449,529 A | 5/1984 | Burns et al. |
| 4,449,974 A | 5/1984 | Messingschlager |
| 4,457,757 A | 7/1984 | Molteno |
| 4,501,274 A | 2/1985 | Skjaerpe |
| 4,554,918 A | 11/1985 | White |
| 4,560,383 A | 12/1985 | Leiske |
| 4,578,058 A | 3/1986 | Grandon |
| 4,604,087 A | 8/1986 | Joseph |
| 4,632,842 A | 12/1986 | Karwoski et al. |
| 4,634,418 A | 1/1987 | Binder |
| 4,642,090 A | 2/1987 | Ultrata |
| 4,692,142 A | 9/1987 | Dignam et al. |
| 4,718,907 A | 1/1988 | Karwoski et al. |
| 4,722,724 A | 2/1988 | Schocket |
| 4,733,665 A | 3/1988 | Palmaz |
| 4,750,901 A | 6/1988 | Molteno |
| 4,782,819 A | 11/1988 | Adair |
| 4,787,885 A | 11/1988 | Binder |
| 4,800,870 A | 1/1989 | Reid, Jr. |
| 4,800,890 A | 1/1989 | Cramer |
| 4,804,382 A | 2/1989 | Turina et al. |
| 4,820,626 A | 4/1989 | Williams et al. |
| 4,826,478 A | 5/1989 | Schocket |
| 4,846,172 A | 7/1989 | Berlin |
| 4,846,793 A | 7/1989 | Leonard et al. |
| 4,867,173 A | 9/1989 | Leoni |
| 4,870,953 A | 10/1989 | DonMichael et al. |
| 4,886,488 A | 12/1989 | White |
| 4,900,300 A | 2/1990 | Lee |
| 4,905,667 A | 3/1990 | Foerster et al. |
| 4,936,825 A | 6/1990 | Ungerleider |
| 4,946,436 A | 8/1990 | Smith |
| 4,968,296 A | 11/1990 | Ritch et al. |
| 4,986,810 A | 1/1991 | Semrad |
| 4,991,602 A | 2/1991 | Amplatz et al. |
| 5,005,577 A | 4/1991 | Frenekl |
| 5,041,081 A | 8/1991 | Odrich |
| 5,053,040 A | 10/1991 | Goldsmith, III |
| 5,053,044 A | 10/1991 | Mueller et al. |
| 5,073,163 A | 12/1991 | Lippman |
| 5,092,837 A | 3/1992 | Ritch et al. |
| 5,095,887 A | 3/1992 | Leon et al. |
| 5,116,327 A | 5/1992 | Seder et al. |
| 5,127,901 A | 7/1992 | Odrich |
| 5,129,895 A | 7/1992 | Vassiliadis et al. |
| 5,139,502 A | 8/1992 | Berg et al. |
| 5,169,386 A | 12/1992 | Becker et al. |
| 5,171,213 A | 12/1992 | Price, Jr. |
| 5,178,604 A | 1/1993 | Baerveldt et al. |
| 5,180,362 A | 1/1993 | Worst |
| 5,207,685 A | 5/1993 | Cinberg et al. |
| 5,221,255 A | 6/1993 | Mahurkar et al. |
| 5,246,451 A | 9/1993 | Trescony et al. |
| 5,248,231 A | 9/1993 | Denham et al. |
| 5,284,476 A | 2/1994 | Koch |
| 5,290,295 A | 3/1994 | Querals et al. |
| 5,300,020 A | 4/1994 | L'Esperance, Jr. |
| 5,318,513 A | 6/1994 | Leib et al. |
| 5,324,306 A | 6/1994 | Makower et al. |
| 5,326,345 A | 7/1994 | Price, Jr. |
| 5,334,137 A | 8/1994 | Freeman |
| 5,338,291 A | 8/1994 | Speckman et al. |
| 5,342,370 A | 8/1994 | Simon et al. |
| 5,346,464 A | 9/1994 | Camras |
| 5,358,492 A | 10/1994 | Feibus |
| 5,360,399 A | 11/1994 | Stegmann |
| 5,370,607 A | 12/1994 | Memmen |
| 5,370,641 A | 12/1994 | O'Donnell, Jr. |
| 5,372,577 A | 12/1994 | Ungerleider |
| 5,380,290 A | 1/1995 | Makower et al. |
| 5,397,300 A | 3/1995 | Baerveldt et al. |
| 5,415,666 A | 5/1995 | Gourlay et al. |
| 5,433,701 A | 7/1995 | Rubinstein |
| 5,445,637 A | 8/1995 | Bretton |
| 5,454,796 A | 10/1995 | Krupin |
| 5,462,558 A | 10/1995 | Kolesa et al. |
| 5,472,440 A | 12/1995 | Beckman |
| 5,476,445 A | 12/1995 | Baerveldt et al. |
| 5,486,165 A | 1/1996 | Stegmann |
| 5,520,631 A | 5/1996 | Nordquist et al. |
| 5,556,400 A | 9/1996 | Tunis |
| 5,558,629 A | 9/1996 | Baerveldt et al. |
| 5,558,630 A | 9/1996 | Fisher |
| 5,558,637 A | 9/1996 | Allonen et al. |
| 5,562,641 A | 10/1996 | Flomenblit et al. |
| RE35,390 E | 12/1996 | Smith |
| 5,626,558 A | 5/1997 | Suson |
| 5,626,559 A | 5/1997 | Solomon |
| 5,639,278 A | 6/1997 | Dereume et al. |
| 5,643,321 A | 7/1997 | McDevitt |
| 5,651,782 A | 7/1997 | Simon et al. |
| 5,651,783 A | 7/1997 | Reynard |
| 5,653,724 A | 8/1997 | Imonti |
| 5,669,501 A | 9/1997 | Hissong et al. |
| 5,676,679 A | 10/1997 | Simon et al. |
| 5,681,275 A | 10/1997 | Ahmed |
| 5,681,323 A | 10/1997 | Arick |
| 5,695,479 A | 12/1997 | Jagpal |
| 5,702,414 A | 12/1997 | Richter et al. |
| 5,702,419 A | 12/1997 | Berry et al. |
| 5,704,907 A | 1/1998 | Nordquist et al. |
| 5,713,844 A | 2/1998 | Peyman |
| 5,722,948 A | 3/1998 | Gross |
| 5,723,005 A | 3/1998 | Herrick |

(56) References Cited

U.S. PATENT DOCUMENTS

| | | |
|---|---|---|
| 5,725,529 A | 3/1998 | Nicholson et al. |
| 5,725,546 A | 3/1998 | Samson |
| 5,733,256 A | 3/1998 | Costin |
| 5,741,292 A | 4/1998 | Mendius |
| 5,741,333 A | 4/1998 | Frid |
| 5,743,868 A | 4/1998 | Brown et al. |
| 5,752,928 A | 5/1998 | de Roulhac et al. |
| 5,762,625 A | 6/1998 | Igaki |
| 5,766,243 A | 6/1998 | Christensen et al. |
| 5,785,674 A | 7/1998 | Mateen |
| 5,792,099 A | 8/1998 | DeCamp et al. |
| 5,800,376 A | 9/1998 | Vaskelis |
| 5,807,244 A | 9/1998 | Barot |
| 5,807,302 A | 9/1998 | Wandel |
| 5,810,870 A | 9/1998 | Myers et al. |
| 5,817,100 A | 10/1998 | Igaki |
| 5,824,071 A | 10/1998 | Nelson et al. |
| 5,830,171 A | 11/1998 | Wallace |
| 5,833,694 A | 11/1998 | Poncet |
| 5,836,939 A | 11/1998 | Negus et al. |
| 5,846,199 A | 12/1998 | Hijlkema et al. |
| 5,865,831 A | 2/1999 | Cozean et al. |
| 5,868,697 A | 2/1999 | Ritcher et al. |
| 5,879,319 A | 3/1999 | Pynson et al. |
| 5,882,327 A | 3/1999 | Jacob |
| 5,891,084 A | 4/1999 | Lee |
| 5,893,837 A | 4/1999 | Eagles et al. |
| 5,908,449 A | 6/1999 | Bruchman et al. |
| 5,913,852 A | 6/1999 | Magram |
| 5,927,585 A | 7/1999 | Moorman et al. |
| 5,932,299 A | 8/1999 | Katoot |
| 5,941,250 A | 8/1999 | Aramant et al. |
| 5,980,548 A | 11/1999 | Evans |
| 5,984,913 A | 11/1999 | Kritzinger et al. |
| 6,004,302 A | 12/1999 | Brierley |
| 6,007,510 A | 12/1999 | Nigam |
| 6,007,511 A | 12/1999 | Prywes |
| 6,030,416 A | 2/2000 | Huo et al. |
| 6,033,434 A | 3/2000 | Borghi |
| 6,036,678 A | 3/2000 | Giungo |
| 6,036,682 A | 3/2000 | Lange et al. |
| 6,045,557 A | 4/2000 | White et al. |
| 6,050,970 A | 4/2000 | Baerveldt |
| 6,050,999 A | 4/2000 | Paraschac et al. |
| 6,071,286 A | 6/2000 | Mawad |
| 6,074,395 A | 6/2000 | Trott et al. |
| 6,077,299 A | 6/2000 | Adelberg et al. |
| 6,102,045 A | 8/2000 | Nordquist et al. |
| 6,135,977 A | 10/2000 | Drasler et al. |
| 6,142,990 A | 11/2000 | Burk |
| 6,146,387 A | 11/2000 | Trott et al. |
| 6,165,210 A | 12/2000 | Lau et al. |
| 6,168,575 B1 | 1/2001 | Soltanpour |
| 6,174,305 B1 | 1/2001 | Mikus et al. |
| 6,186,974 B1 | 2/2001 | Allan et al. |
| 6,187,016 B1 | 2/2001 | Hedges et al. |
| 6,203,513 B1 | 3/2001 | Yaron et al. |
| 6,221,078 B1 | 4/2001 | Bylsma |
| 6,224,570 B1 | 5/2001 | Le et al. |
| 6,231,597 B1 | 5/2001 | Deem et al. |
| 6,241,721 B1 | 6/2001 | Cozean et al. |
| 6,254,612 B1 | 7/2001 | Hieshima |
| 6,261,256 B1 | 7/2001 | Ahmed |
| 6,264,668 B1 | 7/2001 | Prywes |
| 6,287,313 B1 | 9/2001 | Sasso |
| 6,299,603 B1 | 10/2001 | Hecker et al. |
| 6,306,114 B1 | 10/2001 | Freeman et al. |
| 6,342,058 B1 | 1/2002 | Portney |
| 6,355,033 B1 | 3/2002 | Moorman et al. |
| 6,358,222 B1 | 3/2002 | Grundei |
| 6,361,519 B1 | 3/2002 | Knudson et al. |
| 6,363,938 B2 | 4/2002 | Saadat |
| 6,375,642 B1 | 4/2002 | Grieshaber et al. |
| 6,378,526 B1 | 4/2002 | Bowman et al. |
| 6,402,734 B1 | 6/2002 | Weiss |
| 6,405,732 B1 | 6/2002 | Edwards et al. |
| 6,428,501 B1 | 8/2002 | Reynard |
| 6,428,566 B1 | 8/2002 | Holt |
| 6,450,937 B1 | 9/2002 | Mercereau et al. |
| 6,450,984 B1 | 9/2002 | Lynch et al. |
| 6,454,787 B1 | 9/2002 | Maddalo et al. |
| 6,464,724 B1 | 10/2002 | Lynch et al. |
| 6,468,283 B1 | 10/2002 | Richter et al. |
| 6,494,857 B1 | 12/2002 | Neuhann |
| 6,508,779 B1 | 1/2003 | Suson |
| 6,524,275 B1 | 2/2003 | Lynch et al. |
| 6,530,896 B1 | 3/2003 | Elliott |
| 6,533,768 B1 | 3/2003 | Hill |
| 6,544,249 B1 | 4/2003 | Yu et al. |
| 6,561,974 B1 | 5/2003 | Grieshaber et al. |
| 6,582,426 B2 | 6/2003 | Moorman et al. |
| 6,582,453 B1 | 6/2003 | Tran et al. |
| 6,585,680 B2 | 7/2003 | Bugge |
| 6,585,753 B2 | 7/2003 | Eder et al. |
| 6,589,198 B1 | 7/2003 | Soltanpour et al. |
| 6,589,203 B1 | 7/2003 | Mitrev |
| 6,595,945 B2 | 7/2003 | Brown |
| 6,605,053 B1 | 8/2003 | Kamm et al. |
| 6,607,542 B1 | 8/2003 | Wild |
| 6,613,343 B2 | 9/2003 | Dillingham et al. |
| 6,620,154 B1 | 9/2003 | Amirkhanian et al. |
| 6,623,283 B1 | 9/2003 | Torigian et al. |
| 6,626,858 B2 | 9/2003 | Lynch et al. |
| 6,629,981 B2 | 10/2003 | Bui et al. |
| 6,638,239 B1 | 10/2003 | Bergheim et al. |
| 6,666,213 B2 | 12/2003 | Svadovskiy |
| 6,666,841 B2 | 12/2003 | Gharib et al. |
| 6,676,607 B2 | 1/2004 | De Juan, Jr. et al. |
| 6,682,500 B2 | 1/2004 | Soltanpour et al. |
| 6,699,211 B2 | 3/2004 | Savage |
| 6,699,272 B2 | 3/2004 | Slepian et al. |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,763,833 B1 | 7/2004 | Khera et al. |
| 6,764,439 B2 | 7/2004 | Schaaf et al. |
| 6,767,346 B2 | 7/2004 | Damasco et al. |
| 6,780,164 B2 | 8/2004 | Bergheim et al. |
| 6,780,165 B2 | 8/2004 | Kadziauskas et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,827,738 B2 | 12/2004 | Willis et al. |
| 6,893,413 B2 | 5/2005 | Martin |
| 6,902,577 B2 | 6/2005 | Lipshitz et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen |
| 6,981,958 B1 | 1/2006 | Gharib et al. |
| 7,077,821 B2 | 7/2006 | Durgin |
| 7,077,848 B1 | 7/2006 | Juan et al. |
| 7,090,681 B2 | 8/2006 | Weber et al. |
| 7,094,225 B2 | 8/2006 | Tu et al. |
| 7,101,402 B2 | 9/2006 | Phelps et al. |
| 7,135,009 B2 | 11/2006 | Tu et al. |
| 7,135,016 B1 | 11/2006 | Asia et al. |
| 7,144,616 B1 | 12/2006 | Unger et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,192,484 B2 | 3/2007 | Chappa et al. |
| 7,217,263 B2 | 5/2007 | Humayun et al. |
| 7,220,238 B2 | 5/2007 | Lynch et al. |
| 7,273,475 B2 | 9/2007 | Tu et al. |
| 7,294,115 B1 | 11/2007 | Wilk |
| 7,297,130 B2 | 11/2007 | Bergheim et al. |
| 7,331,984 B2 | 2/2008 | Tu et al. |
| 7,344,528 B1 | 3/2008 | Tu et al. |
| 7,364,564 B2 | 4/2008 | Sniegowski et al. |
| 7,431,710 B2 | 10/2008 | Tu et al. |
| 7,468,065 B2 | 12/2008 | Weber et al. |
| 7,488,303 B1 | 2/2009 | Haffner et al. |

(56) References Cited

U.S. PATENT DOCUMENTS

| | | |
|---|---|---|
| 7,520,876 B2 | 4/2009 | Reesemann et al. |
| D592,746 S | 5/2009 | Highley et al. |
| RE40,722 E | 6/2009 | Chappa |
| 7,563,241 B2 | 7/2009 | Tu et al. |
| D606,190 S | 12/2009 | Pruitt et al. |
| 7,641,627 B2 | 1/2010 | Camras et al. |
| 7,678,065 B2 | 3/2010 | Haffner et al. |
| 7,695,135 B1 | 4/2010 | Rosenthal |
| 7,708,711 B2 | 5/2010 | Tu et al. |
| 7,713,228 B2 | 5/2010 | Robin |
| 7,758,624 B2 | 7/2010 | Dom et al. |
| 7,771,388 B2 | 8/2010 | Olsen et al. |
| 7,811,268 B2 | 10/2010 | Maldon Ado Bas |
| 7,850,637 B2 | 12/2010 | Lynch et al. |
| 7,857,782 B2 | 12/2010 | Tu et al. |
| 7,862,531 B2 | 1/2011 | Yaron et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,905,904 B2 | 3/2011 | Stone et al. |
| 7,931,660 B2 | 4/2011 | Aranyi et al. |
| 7,945,336 B2 | 5/2011 | Sauter/Starace et al. |
| 7,951,155 B2 | 5/2011 | Smedley et al. |
| 7,959,632 B2 | 6/2011 | Fugo |
| 7,967,772 B2 | 6/2011 | Mckenzie et al. |
| 7,997,460 B2 | 8/2011 | Pardes et al. |
| 8,007,459 B2 | 8/2011 | Haffner et al. |
| D645,489 S | 9/2011 | Gille et al. |
| D645,490 S | 9/2011 | Gille et al. |
| 8,034,016 B2 | 10/2011 | Yaron et al. |
| 8,034,105 B2 | 10/2011 | Stegmann et al. |
| 8,062,244 B2 | 11/2011 | Tu et al. |
| 8,070,290 B2 | 12/2011 | Gille et al. |
| 8,075,511 B2 | 12/2011 | Tu et al. |
| 8,118,768 B2 | 2/2012 | Tu et al. |
| 8,142,364 B2 | 3/2012 | Haffner et al. |
| 8,152,752 B2 | 4/2012 | Lynch et al. |
| 8,197,418 B2 | 6/2012 | Lal et al. |
| 8,267,882 B2 | 9/2012 | Euteneuer et al. |
| 8,267,995 B2 | 9/2012 | Castillejos |
| 8,273,050 B2 | 9/2012 | Bergheim et al. |
| 8,333,742 B2 | 12/2012 | Bergheim et al. |
| 8,337,445 B2 | 12/2012 | Tu et al. |
| 8,348,877 B2 | 1/2013 | Tu et al. |
| 8,388,568 B2 | 3/2013 | Lynch et al. |
| 8,414,518 B2 | 4/2013 | Schieber et al. |
| 8,419,673 B2 | 4/2013 | Rickard |
| 8,425,449 B2 | 4/2013 | Wardle et al. |
| 8,439,972 B2 | 5/2013 | Badawi et al. |
| 8,506,515 B2 | 8/2013 | Burns et al. |
| 8,540,659 B2 | 9/2013 | Berlin |
| 8,545,431 B2 | 10/2013 | Rickard |
| 8,579,846 B2 | 11/2013 | Tu et al. |
| 8,579,848 B2 | 11/2013 | Field et al. |
| 8,585,631 B2 | 11/2013 | Dacquay |
| 8,585,664 B2 | 11/2013 | Dos Santos et al. |
| 8,603,024 B2 | 12/2013 | Bohm et al. |
| 8,617,094 B2 | 12/2013 | Smedley et al. |
| 8,656,958 B2 | 2/2014 | Unger et al. |
| 8,679,089 B2 | 3/2014 | Berlin |
| 8,721,580 B2 | 5/2014 | Rickard et al. |
| 8,753,305 B2 | 6/2014 | Field et al. |
| 8,771,217 B2 | 7/2014 | Lynch et al. |
| 8,771,220 B2 | 7/2014 | Nissan |
| 8,801,648 B2 | 8/2014 | Bergheim et al. |
| 8,808,219 B2 | 8/2014 | Bergheim et al. |
| 8,808,222 B2 | 8/2014 | Schieber et al. |
| 8,808,224 B2 | 8/2014 | Rickard |
| 8,814,820 B2 | 8/2014 | Bergheim et al. |
| 8,840,578 B2 | 9/2014 | Dos Santos et al. |
| 8,852,137 B2 | 10/2014 | Horvath et al. |
| 8,852,266 B2 | 10/2014 | Brooks et al. |
| 8,864,701 B2 | 10/2014 | Dos Santos et al. |
| 8,882,781 B2 | 11/2014 | Smedley et al. |
| 8,956,320 B2 | 2/2015 | Ovchinnikov et al. |
| 8,986,240 B2 | 3/2015 | Dos Santos et al. |
| 8,998,838 B2 | 4/2015 | Yalamanchili |
| 8,998,983 B2 | 4/2015 | Auld |
| 9,066,782 B2 | 6/2015 | Tu et al. |
| 9,072,588 B2 | 7/2015 | Bohm et al. |
| 9,125,721 B2 | 9/2015 | Field |
| 9,132,034 B2 | 9/2015 | Dos Santos |
| 9,155,653 B2 | 10/2015 | Field |
| 9,155,654 B2 | 10/2015 | Tu et al. |
| 9,173,775 B2 | 11/2015 | Haffner et al. |
| 9,220,632 B2 | 12/2015 | Smedley et al. |
| 9,226,851 B2 | 1/2016 | Gunn |
| 9,283,115 B2 | 3/2016 | Lind et al. |
| 9,289,324 B2 | 3/2016 | Johnson et al. |
| 9,301,875 B2 | 4/2016 | Tu et al. |
| 9,492,320 B2 | 11/2016 | Lynch et al. |
| 9,554,940 B2 | 1/2017 | Haffner et al. |
| 9,561,131 B2 | 2/2017 | Tu et al. |
| 9,572,963 B2 | 2/2017 | Tu et al. |
| 9,592,151 B2 | 3/2017 | Rangel-Friedman et al. |
| 9,597,230 B2 | 3/2017 | Haffner et al. |
| 9,603,738 B2 | 3/2017 | Haffner et al. |
| 9,603,741 B2 | 3/2017 | Berlin |
| 9,636,255 B2 | 5/2017 | Haffner et al. |
| 9,668,915 B2 | 6/2017 | Haffner et al. |
| 9,730,638 B2 | 8/2017 | Haffner et al. |
| 9,789,001 B2 | 10/2017 | Tu et al. |
| 9,827,143 B2 | 11/2017 | Lynch et al. |
| 9,833,357 B2 | 12/2017 | Berlin |
| 9,849,027 B2 | 12/2017 | Highley et al. |
| 9,962,290 B2 | 5/2018 | Burns et al. |
| 9,987,472 B2 | 6/2018 | Tu et al. |
| 9,993,368 B2 | 6/2018 | Bergheim et al. |
| D833,008 S | 11/2018 | Kalina, Jr. et al. |
| 10,159,601 B2 | 12/2018 | Berlin |
| 10,188,551 B2 | 1/2019 | Rangel-Friedman et al. |
| 10,206,813 B2 | 2/2019 | Haffner et al. |
| D846,738 S | 4/2019 | Kalina, Jr. et al. |
| 10,245,178 B1 | 4/2019 | Heitzmann et al. |
| 10,271,989 B2 | 4/2019 | Haffner et al. |
| 10,285,853 B2 | 5/2019 | Rangel-Friedman et al. |
| 10,285,856 B2 | 5/2019 | Tu et al. |
| 10,406,029 B2 | 9/2019 | Tu et al. |
| 10,485,701 B2 | 11/2019 | Haffner et al. |
| 10,485,702 B2 | 11/2019 | Bergheim et al. |
| 10,492,950 B2 | 12/2019 | Lynch et al. |
| 10,499,809 B2 | 12/2019 | Kalina, Jr. et al. |
| 10,517,759 B2 | 12/2019 | Grimaldi et al. |
| 10,568,762 B2 | 2/2020 | Lynch et al. |
| D886,997 S | 6/2020 | Kalina, Jr. et al. |
| 10,674,906 B2 | 6/2020 | Kalina, Jr. et al. |
| 10,813,789 B2 | 10/2020 | Haffner et al. |
| D901,683 S | 11/2020 | Kalina, Jr. et al. |
| 10,828,195 B2 | 11/2020 | Burns et al. |
| 10,828,473 B2 | 11/2020 | Haffner et al. |
| 10,959,941 B2 | 3/2021 | Haffner |
| 11,019,996 B2 | 6/2021 | Kalina, Jr. et al. |
| 11,019,997 B2 | 6/2021 | Kalina, Jr. et al. |
| 11,116,625 B2 | 9/2021 | Kalina, Jr. |
| D938,585 S | 12/2021 | Kalina, Jr. et al. |
| 11,197,780 B2 | 12/2021 | Haffner et al. |
| 11,253,394 B2 | 2/2022 | Haffner et al. |
| 11,318,043 B2 | 5/2022 | Heitzmann et al. |
| 11,376,040 B2 | 7/2022 | Kalina, Jr. et al. |
| 11,426,306 B2 | 8/2022 | Haffner et al. |
| 11,523,938 B2 | 12/2022 | Rangel-Friedman et al. |
| 11,559,430 B2 | 1/2023 | Crimaldi et al. |
| 11,564,833 B2 | 1/2023 | Burns et al. |
| 11,744,458 B2 | 9/2023 | Kalina, Jr. et al. |
| 2001/0000527 A1 | 4/2001 | Yaron et al. |
| 2001/0025150 A1 | 9/2001 | de Juan et al. |
| 2001/0053873 A1 | 12/2001 | Schaaf et al. |
| 2002/0013546 A1 | 1/2002 | Grieshaber et al. |
| 2002/0013572 A1 | 1/2002 | Berlin |
| 2002/0026200 A1 | 2/2002 | Savage |
| 2002/0052640 A1 | 5/2002 | Bigus et al. |
| 2002/0072673 A1 | 6/2002 | Yamamoto et al. |
| 2002/0082591 A1 | 6/2002 | Haefliger |

(56) References Cited

U.S. PATENT DOCUMENTS

| | | |
|---|---|---|
| 2002/0087111 A1 | 7/2002 | Ethier et al. |
| 2002/0099434 A1 | 7/2002 | Buscemi et al. |
| 2002/0111608 A1 | 8/2002 | Baerveldt et al. |
| 2002/0120284 A1 | 8/2002 | Schachar et al. |
| 2002/0120285 A1 | 8/2002 | Schachar et al. |
| 2002/0133168 A1 | 9/2002 | Smedley et al. |
| 2002/0143284 A1 | 10/2002 | Tu et al. |
| 2002/0156413 A1 | 10/2002 | Williams et al. |
| 2002/0165522 A1 | 11/2002 | Holmen |
| 2002/0169468 A1 | 11/2002 | Brown |
| 2002/0177856 A1 | 11/2002 | Richter et al. |
| 2002/0188308 A1 | 12/2002 | Tu et al. |
| 2002/0193725 A1 | 12/2002 | Odrich |
| 2003/0014021 A1 | 1/2003 | Holmen |
| 2003/0014092 A1 | 1/2003 | Neuhann |
| 2003/0019833 A1 | 1/2003 | Unger et al. |
| 2003/0055372 A1 | 3/2003 | Lynch et al. |
| 2003/0060752 A1 | 3/2003 | Bergheim et al. |
| 2003/0079329 A1 | 5/2003 | Yaron et al. |
| 2003/0088260 A1 | 5/2003 | Smedley et al. |
| 2003/0093084 A1 | 5/2003 | Nissan et al. |
| 2003/0097117 A1 | 5/2003 | Buono |
| 2003/0097151 A1 | 5/2003 | Smedley et al. |
| 2003/0105456 A1 | 6/2003 | Lin |
| 2003/0109907 A1 | 6/2003 | Shadduck |
| 2003/0135149 A1 | 7/2003 | Cullen et al. |
| 2003/0139729 A1 | 7/2003 | Stegmann et al. |
| 2003/0153863 A1 | 8/2003 | Patel |
| 2003/0181848 A1 | 9/2003 | Bergheim et al. |
| 2003/0187384 A1 | 10/2003 | Bergheim et al. |
| 2003/0195438 A1 | 10/2003 | Petillo |
| 2003/0208163 A1 | 11/2003 | Yaron et al. |
| 2003/0208217 A1 | 11/2003 | Dan |
| 2003/0212383 A1 | 11/2003 | Cote et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0059248 A1 | 3/2004 | Messner et al. |
| 2004/0076676 A1 | 4/2004 | Tojo et al. |
| 2004/0076868 A1 | 4/2004 | Tojo et al. |
| 2004/0088048 A1 | 5/2004 | Richter et al. |
| 2004/0092856 A1 | 5/2004 | Dahan |
| 2004/0098122 A1 | 5/2004 | Lee et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0154946 A1 | 8/2004 | Solovay et al. |
| 2004/0162545 A1 | 8/2004 | Brown et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0215126 A1 | 10/2004 | Ahmed |
| 2004/0216749 A1 | 11/2004 | Tu |
| 2004/0236343 A1 | 11/2004 | Taylor et al. |
| 2004/0243227 A1 | 12/2004 | Starksen et al. |
| 2004/0249404 A1 | 12/2004 | Haefliger |
| 2004/0254517 A1 | 12/2004 | Quiroz/Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260227 A1 | 12/2004 | Lisk, Jr. et al. |
| 2004/0260228 A1 | 12/2004 | Lynch et al. |
| 2005/0038498 A1 | 2/2005 | Dubrow et al. |
| 2005/0049578 A1 | 3/2005 | Tu et al. |
| 2005/0055075 A1 | 3/2005 | Pinchuk et al. |
| 2005/0096639 A1 | 5/2005 | Slatkine et al. |
| 2005/0119601 A9 | 6/2005 | Lynch et al. |
| 2005/0119737 A1 | 6/2005 | Bene et al. |
| 2005/0125003 A1 | 6/2005 | Pinchuk et al. |
| 2005/0165385 A1 | 7/2005 | Simon |
| 2005/0171507 A1 | 8/2005 | Christian et al. |
| 2005/0171562 A1 | 8/2005 | Criscuolo et al. |
| 2005/0182350 A1 | 8/2005 | Nigam |
| 2005/0184004 A1 | 8/2005 | Rodgers et al. |
| 2005/0192527 A1 | 9/2005 | Gharib et al. |
| 2005/0209549 A1 | 9/2005 | Bergheim et al. |
| 2005/0209672 A1 | 9/2005 | George et al. |
| 2005/0240143 A1 | 10/2005 | Dohlman |
| 2005/0240222 A1 | 10/2005 | Shipp |
| 2005/0250788 A1 | 11/2005 | Tu et al. |
| 2005/0261624 A1 | 11/2005 | Wilcox |
| 2005/0267397 A1 | 12/2005 | Bhalla |
| 2005/0267398 A1 | 12/2005 | Protopsaltis et al. |
| 2005/0267478 A1 | 12/2005 | Corradi et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2006/0032507 A1 | 2/2006 | Tu |
| 2006/0036207 A1 | 2/2006 | Koonmen et al. |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0129129 A1 | 6/2006 | Smith |
| 2006/0155300 A1 | 7/2006 | Stamper et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0210605 A1 | 9/2006 | Chang et al. |
| 2006/0217741 A1 | 9/2006 | Ghannoum |
| 2006/0235367 A1 | 10/2006 | Takashima et al. |
| 2006/0241580 A1 | 10/2006 | Mittelstein et al. |
| 2006/0241749 A1 | 10/2006 | Tu et al. |
| 2006/0276738 A1 | 12/2006 | Becker |
| 2006/0276739 A1 | 12/2006 | Brown |
| 2007/0004998 A1 | 1/2007 | Rodgers et al. |
| 2007/0021653 A1 | 1/2007 | Hattenbach et al. |
| 2007/0073275 A1 | 3/2007 | Conston et al. |
| 2007/0073390 A1 | 3/2007 | Lee |
| 2007/0078371 A1 | 4/2007 | Brown et al. |
| 2007/0078471 A1 | 4/2007 | Schachar et al. |
| 2007/0088432 A1 | 4/2007 | Solovay et al. |
| 2007/0093740 A1 | 4/2007 | Shetty |
| 2007/0106199 A1 | 5/2007 | Krivoy et al. |
| 2007/0106200 A1 | 5/2007 | Levy |
| 2007/0118065 A1 | 5/2007 | Pinchuk et al. |
| 2007/0118066 A1 | 5/2007 | Pinchuk et al. |
| 2007/0123812 A1 | 5/2007 | Pinchuk et al. |
| 2007/0123919 A1 | 5/2007 | Schachar et al. |
| 2007/0149927 A1 | 6/2007 | Itou et al. |
| 2007/0154621 A1 | 7/2007 | Raad |
| 2007/0156079 A1 | 7/2007 | Brown |
| 2007/0161981 A1 | 7/2007 | Sanders et al. |
| 2007/0179426 A1 | 8/2007 | Selden |
| 2007/0179471 A1 | 8/2007 | Christian et al. |
| 2007/0185468 A1 | 8/2007 | Prywes |
| 2007/0191863 A1 | 8/2007 | De Juan, Jr. et al. |
| 2007/0207186 A1 | 9/2007 | Scanlon et al. |
| 2007/0212386 A1 | 9/2007 | Patravale et al. |
| 2007/0212387 A1 | 9/2007 | Patravale et al. |
| 2007/0212388 A1 | 9/2007 | Patravale et al. |
| 2007/0212393 A1 | 9/2007 | Patravale et al. |
| 2007/0219632 A1 | 9/2007 | Castillejos |
| 2007/0260201 A1 | 11/2007 | Prausnitz et al. |
| 2007/0276315 A1 | 11/2007 | Haffner |
| 2007/0282244 A1 | 12/2007 | Tu et al. |
| 2007/0282245 A1 | 12/2007 | Tu et al. |
| 2007/0287958 A1 | 12/2007 | McKenzie et al. |
| 2007/0292470 A1 | 12/2007 | Thornton |
| 2007/0292474 A1 | 12/2007 | Hsu et al. |
| 2007/0293807 A1 | 12/2007 | Lynch et al. |
| 2007/0293872 A1 | 12/2007 | Peyman |
| 2007/0293873 A1 | 12/2007 | Chang |
| 2007/0298068 A1 | 12/2007 | Badawi et al. |
| 2008/0027304 A1 | 1/2008 | Pardo et al. |
| 2008/0033351 A1 | 2/2008 | Trogden et al. |
| 2008/0039931 A1 | 2/2008 | Jelle et al. |
| 2008/0045878 A1 | 2/2008 | Bergheim et al. |
| 2008/0051681 A1 | 2/2008 | Schwartz |

(56) References Cited

U.S. PATENT DOCUMENTS

| | | |
|---|---|---|
| 2008/0058704 A1 | 3/2008 | Hee et al. |
| 2008/0082078 A1 | 4/2008 | Berlin |
| 2008/0091224 A1 | 4/2008 | Griffis et al. |
| 2008/0097214 A1 | 4/2008 | Meyers et al. |
| 2008/0097335 A1 | 4/2008 | Trogden et al. |
| 2008/0108932 A1 | 5/2008 | Rodgers |
| 2008/0108933 A1 | 5/2008 | Yu et al. |
| 2008/0108934 A1 | 5/2008 | Berlin |
| 2008/0109037 A1 | 5/2008 | Steiner et al. |
| 2008/0114440 A1 | 5/2008 | Hlavka et al. |
| 2008/0125691 A1 | 5/2008 | Yaron et al. |
| 2008/0140059 A1 | 6/2008 | Schachar et al. |
| 2008/0147083 A1 | 6/2008 | Vold et al. |
| 2008/0147168 A1 | 6/2008 | Ransbury et al. |
| 2008/0161741 A1 | 7/2008 | Bene et al. |
| 2008/0161907 A1 | 7/2008 | Chen et al. |
| 2008/0183289 A1 | 7/2008 | Werblin |
| 2008/0188860 A1 | 8/2008 | Vold |
| 2008/0200860 A1 | 8/2008 | Tu et al. |
| 2008/0200923 A1 | 8/2008 | Beckman et al. |
| 2008/0208176 A1 | 8/2008 | Loh |
| 2008/0210322 A1 | 9/2008 | Unger et al. |
| 2008/0215062 A1 | 9/2008 | Bowen et al. |
| 2008/0221501 A1 | 9/2008 | Cote et al. |
| 2008/0236669 A1 | 10/2008 | Unger et al. |
| 2008/0243156 A1 | 10/2008 | John |
| 2008/0243243 A1 | 10/2008 | Williams et al. |
| 2008/0243247 A1 | 10/2008 | Poley et al. |
| 2008/0255545 A1 | 10/2008 | Mansfield et al. |
| 2008/0269730 A1 | 10/2008 | Dotson |
| 2008/0277007 A1 | 11/2008 | Unger et al. |
| 2008/0281250 A1 | 11/2008 | Bergsneider et al. |
| 2008/0289710 A1 | 11/2008 | Unger et al. |
| 2008/0306429 A1 | 12/2008 | Shields et al. |
| 2009/0036818 A1 | 2/2009 | Grahn et al. |
| 2009/0043242 A1 | 2/2009 | Bene et al. |
| 2009/0043321 A1 | 2/2009 | Conston et al. |
| 2009/0043365 A1 | 2/2009 | Friedland et al. |
| 2009/0076436 A2 | 3/2009 | Gharib et al. |
| 2009/0082860 A1 | 3/2009 | Schieber et al. |
| 2009/0082862 A1 | 3/2009 | Schieber et al. |
| 2009/0082863 A1 | 3/2009 | Schieber et al. |
| 2009/0104248 A1 | 4/2009 | Rapacki et al. |
| 2009/0112245 A1 | 4/2009 | Haefliger |
| 2009/0124973 A1 | 5/2009 | D'Agostino et al. |
| 2009/0132040 A1 | 5/2009 | Frion et al. |
| 2009/0137989 A1 | 5/2009 | Kataoka |
| 2009/0137992 A1 | 5/2009 | Mallakrishnan |
| 2009/0151422 A1 | 6/2009 | Unger et al. |
| 2009/0177138 A1 | 7/2009 | Brown et al. |
| 2009/0182421 A1 | 7/2009 | Silvestrini et al. |
| 2009/0198213 A1 | 8/2009 | Tanaka |
| 2009/0204053 A1 | 8/2009 | Nissan et al. |
| 2009/0227933 A1 | 9/2009 | Karageoziar |
| 2009/0227934 A1 | 9/2009 | Eutenever et al. |
| 2009/0264813 A1 | 10/2009 | Chang |
| 2009/0275924 A1 | 11/2009 | Lattanzio et al. |
| 2009/0287136 A1 | 11/2009 | Castillejos |
| 2009/0287233 A1 | 11/2009 | Huculak |
| 2009/0326432 A1 | 12/2009 | Schmidt et al. |
| 2010/0004635 A1 | 1/2010 | Lin et al. |
| 2010/0025613 A1 | 2/2010 | Tai et al. |
| 2010/0042209 A1 | 2/2010 | Guarnieri |
| 2010/0056977 A1 | 3/2010 | Wandel |
| 2010/0056979 A1 | 3/2010 | Smedley et al. |
| 2010/0057055 A1 | 3/2010 | Camras et al. |
| 2010/0114006 A1 | 5/2010 | Baerveldt |
| 2010/0121342 A1 | 5/2010 | Schieber et al. |
| 2010/0125237 A1 | 5/2010 | Schocket |
| 2010/0168644 A1 | 7/2010 | Brown |
| 2010/0175767 A1 | 7/2010 | Unger et al. |
| 2010/0185138 A1 | 7/2010 | Yaron et al. |
| 2010/0191103 A1 | 7/2010 | Stamper et al. |
| 2010/0191329 A1 | 7/2010 | Badawi et al. |
| 2010/0222733 A1 | 9/2010 | Schieber et al. |
| 2010/0234791 A1 | 9/2010 | Lynch et al. |
| 2010/0241046 A1 | 9/2010 | Pinchuk et al. |
| 2010/0249691 A1 | 9/2010 | Van der Mooren et al. |
| 2010/0274259 A1 | 10/2010 | Yaron et al. |
| 2011/0009874 A1 | 1/2011 | Wardle et al. |
| 2011/0009958 A1 | 1/2011 | Wardle et al. |
| 2011/0046536 A1 | 2/2011 | Stegmann et al. |
| 2011/0046728 A1 | 2/2011 | Shareef et al. |
| 2011/0066098 A1 | 3/2011 | Stergiopulos |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0086095 A1 | 4/2011 | Jacob et al. |
| 2011/0098627 A1 | 4/2011 | Wilcox |
| 2011/0098809 A1 | 4/2011 | Wardle et al. |
| 2011/0118649 A1 | 5/2011 | Stegmann et al. |
| 2011/0118835 A1 | 5/2011 | Silvestrini et al. |
| 2011/0130831 A1 | 6/2011 | Badawi et al. |
| 2011/0144559 A1 | 6/2011 | Lafdi et al. |
| 2011/0196487 A1 | 8/2011 | Badawi et al. |
| 2011/0224597 A1 | 9/2011 | Stegmann et al. |
| 2011/0244014 A1 | 10/2011 | Williams et al. |
| 2011/0245753 A1 | 10/2011 | Sunalp |
| 2011/0248671 A1 | 10/2011 | Dos Santos et al. |
| 2011/0257623 A1 | 10/2011 | Marshall et al. |
| 2011/0319806 A1 | 12/2011 | Wardle |
| 2012/0010702 A1 | 1/2012 | Stegmann et al. |
| 2012/0022424 A1 | 1/2012 | Yamamoto et al. |
| 2012/0035524 A1 | 2/2012 | Silvestrini |
| 2012/0059338 A1 | 3/2012 | Beeley et al. |
| 2012/0059461 A1 | 3/2012 | Badawi et al. |
| 2012/0078158 A1 | 3/2012 | Haffner et al. |
| 2012/0078362 A1 | 3/2012 | Haffner et al. |
| 2012/0089072 A1 | 4/2012 | Cunningham, Jr. |
| 2012/0089073 A1 | 4/2012 | Cunningham, Jr. |
| 2012/0130467 A1 | 5/2012 | Selden et al. |
| 2012/0179087 A1 | 7/2012 | Schieber et al. |
| 2012/0184892 A1 | 7/2012 | Bigler et al. |
| 2012/0203160 A1 | 8/2012 | Kahook et al. |
| 2012/0257167 A1 | 10/2012 | Gille et al. |
| 2012/0259195 A1 | 10/2012 | Haffner et al. |
| 2012/0289883 A1 | 11/2012 | Meng et al. |
| 2012/0302861 A1 | 11/2012 | Marshall et al. |
| 2012/0310072 A1 | 12/2012 | Grieshaber |
| 2012/0323159 A1 | 12/2012 | Wardle et al. |
| 2013/0006164 A1 | 1/2013 | Yaron et al. |
| 2013/0006165 A1 | 1/2013 | Eutenener et al. |
| 2013/0018295 A1 | 1/2013 | Haffner et al. |
| 2013/0018296 A1 | 1/2013 | Bergheim et al. |
| 2013/0079701 A1 | 3/2013 | Schieber et al. |
| 2013/0090534 A1 | 4/2013 | Burns et al. |
| 2013/0102949 A1 | 4/2013 | Baerveldt |
| 2013/0144202 A1 | 6/2013 | Field et al. |
| 2013/0150770 A1 | 6/2013 | Horvath et al. |
| 2013/0150773 A1 | 6/2013 | Nissan et al. |
| 2013/0150774 A1 | 6/2013 | Field et al. |
| 2013/0150776 A1 | 6/2013 | Bohm et al. |
| 2013/0150777 A1 | 6/2013 | Bohm et al. |
| 2013/0150779 A1 | 6/2013 | Field |
| 2013/0150959 A1 | 6/2013 | Shieber et al. |
| 2013/0158381 A1 | 6/2013 | Rickard |
| 2013/0158462 A1 | 6/2013 | Wardle et al. |
| 2013/0165840 A1 | 6/2013 | Orge |
| 2013/0172804 A1 | 7/2013 | Schieber et al. |
| 2013/0184631 A1 | 7/2013 | Pinchuk |
| 2013/0245532 A1 | 9/2013 | Tu et al. |
| 2013/0253404 A1 | 9/2013 | Tu |
| 2013/0253405 A1 | 9/2013 | Tu |
| 2013/0281910 A1 | 10/2013 | Tu |
| 2013/0310930 A1 | 11/2013 | Tu et al. |
| 2014/0034607 A1 | 2/2014 | Meng et al. |
| 2014/0046437 A1 | 2/2014 | Renke |
| 2014/0052046 A1 | 2/2014 | Peartree et al. |
| 2014/0243731 A1 | 8/2014 | Rickard et al. |
| 2015/0223981 A1 | 8/2015 | Smedley et al. |
| 2015/0342875 A1 | 12/2015 | Haffner |
| 2015/0374546 A1 | 12/2015 | Hill |

(56) References Cited

U.S. PATENT DOCUMENTS

| | | |
|---|---|---|
| 2016/0045363 A1 | 2/2016 | Haffner et al. |
| 2016/0287438 A1 | 10/2016 | Badawi et al. |
| 2016/0354309 A1 | 12/2016 | Heitzmann et al. |
| 2017/0135857 A1 | 5/2017 | Haffner et al. |
| 2017/0156848 A1 | 6/2017 | Schieber |
| 2018/0021170 A1 | 1/2018 | Haffner et al. |
| 2018/0028361 A1 | 2/2018 | Haffner et al. |
| 2018/0085065 A1 | 3/2018 | Haffner et al. |
| 2018/0104102 A1 | 4/2018 | Lynch et al. |
| 2018/0161205 A1 | 6/2018 | Tu et al. |
| 2018/0177633 A1 | 6/2018 | Haffner et al. |
| 2018/0280194 A1 | 10/2018 | Heitzmann et al. |
| 2018/0303665 A1 | 10/2018 | Heitzmann et al. |
| 2018/0333296 A1 | 11/2018 | Heitzmann et al. |
| 2018/0369017 A1 | 12/2018 | Schieber et al. |
| 2019/0000673 A1 | 1/2019 | Fjield et al. |
| 2019/0021991 A9 | 1/2019 | Heitzmann et al. |
| 2019/0053704 A1 | 2/2019 | Burns et al. |
| 2019/0083307 A1 | 3/2019 | Burns et al. |
| 2019/0083313 A1 | 3/2019 | Berlin |
| 2019/0104936 A1 | 4/2019 | Gunn et al. |
| 2019/0105077 A1 | 4/2019 | Kalina, Jr. et al. |
| 2019/0125581 A1 | 5/2019 | Heitzmann et al. |
| 2019/0224046 A1 | 7/2019 | Heitzmann et al. |
| 2019/0314199 A1 | 10/2019 | Haffner et al. |
| 2019/0321220 A1 | 10/2019 | Rangel-Friedman et al. |
| 2019/0321225 A1 | 10/2019 | Smedley et al. |
| 2020/0155349 A1 | 5/2020 | Haffner et al. |
| 2020/0179171 A1 | 6/2020 | Crimaldi et al. |
| 2020/0367745 A1 | 11/2020 | Kalina, Jr. et al. |
| 2021/0015662 A1 | 1/2021 | Haffner et al. |
| 2021/0137737 A1 | 5/2021 | Burns et al. |
| 2021/0154449 A1 | 5/2021 | Haffner et al. |
| 2021/0298948 A1 | 9/2021 | Haffner et al. |
| 2021/0315806 A1 | 10/2021 | Haffner |
| 2022/0000663 A1 | 1/2022 | Haffner et al. |
| 2022/0015628 A1 | 1/2022 | Kalina, Jr. et al. |
| 2022/0119350 A1 | 4/2022 | Murphy et al. |
| 2022/0233349 A1 | 7/2022 | Haffner et al. |
| 2022/0233354 A1 | 7/2022 | Haffner et al. |
| 2022/0313486 A1 | 10/2022 | Heitzmann et al. |
| 2022/0330979 A1 | 10/2022 | Kalina, Jr. et al. |
| 2023/0053931 A1 | 2/2023 | Haffner et al. |
| 2023/0090539 A1 | 3/2023 | Haffner et al. |
| 2023/0157868 A1 | 5/2023 | Haffner et al. |
| 2023/0210694 A1 | 7/2023 | Crimaldi et al. |
| 2023/0293344 A1 | 9/2023 | Burns et al. |
| 2023/0301830 A1 | 9/2023 | Heitzmann et al. |
| 2023/0372303 A1 | 11/2023 | Liu et al. |

FOREIGN PATENT DOCUMENTS

| | | |
|---|---|---|
| AU | 2004264913 | 12/2011 |
| AU | 2009251058 | 12/2013 |
| CA | 2273331 | 6/1998 |
| CA | 2244646 | 2/1999 |
| CA | 2311244 | 6/1999 |
| CA | 2442652 | 1/2011 |
| CA | 2766131 | 1/2011 |
| CA | 2683224 | 12/2014 |
| CH | 92111244 | 7/1993 |
| DE | 19840047 | 3/2000 |
| DE | 10127666 | 1/2003 |
| EP | 0550791 | 7/1993 |
| EP | 0858788 | 8/1998 |
| EP | 1977724 | 10/2008 |
| EP | 2260803 | 12/2010 |
| EP | 2260804 | 12/2010 |
| EP | 2263621 | 12/2010 |
| EP | 2351589 | 8/2011 |
| EP | 2982354 | 2/2016 |
| EP | 2985012 | 2/2016 |
| EP | 2967993 | 4/2019 |
| FR | 2553658 | 4/1985 |
| FR | 2710269 | 3/1995 |
| FR | 2721499 | 12/1995 |
| FR | 2757068 | 6/1998 |
| GB | 2296663 | 7/1996 |
| JP | 2005-502811 | 5/1993 |
| JP | 2010-248869 | 9/1998 |
| JP | 2011-123205 | 5/1999 |
| JP | 2001-523519 | 11/2001 |
| JP | 2002-541977 | 12/2002 |
| JP | 2001-507969 | 1/2003 |
| JP | 2004-500220 | 1/2004 |
| JP | 2004-518450 | 6/2004 |
| JP | 2005-512607 | 5/2005 |
| JP | 3703721 | 7/2005 |
| JP | 2005-525835 | 9/2005 |
| JP | 2007-501066 | 1/2007 |
| JP | 2007-535386 | 12/2007 |
| JP | 4031836 | 1/2008 |
| JP | 2009-056324 | 3/2009 |
| JP | 2009-523540 | 6/2009 |
| JP | 2009-542370 | 12/2009 |
| JP | 2010-509003 | 3/2010 |
| JP | 2010-533565 | 10/2010 |
| JP | 4688444 | 2/2011 |
| JP | 2011-092765 | 5/2011 |
| JP | 2012-198134 | 9/2012 |
| JP | 2012-527318 | 11/2012 |
| JP | 5255402 | 4/2013 |
| JP | 5323011 | 7/2013 |
| JP | 2013-208434 | 10/2013 |
| JP | 5502811 | 5/2014 |
| JP | 2014-193366 | 10/2014 |
| JP | 2014-240022 | 12/2014 |
| JP | 2016-511108 | 4/2016 |
| JP | 2020-075162 | 5/2020 |
| RU | 2022539 | 11/1994 |
| RU | 2143250 | 12/1999 |
| WO | WO 1989/00869 | 2/1989 |
| WO | WO 1991/08784 | 6/1991 |
| WO | WO 1991/18568 | 12/1991 |
| WO | WO 1992/00112 | 1/1992 |
| WO | WO 1994/13234 | 6/1994 |
| WO | WO 1995/08310 | 3/1995 |
| WO | WO 1998/23237 | 6/1998 |
| WO | WO 1998/030181 | 7/1998 |
| WO | WO 1998/35639 | 8/1998 |
| WO | WO 1998/37831 | 9/1998 |
| WO | WO 1999/26567 | 6/1999 |
| WO | WO 1999/30641 | 6/1999 |
| WO | WO 1999/38470 | 8/1999 |
| WO | WO 2000/13627 | 3/2000 |
| WO | WO 2000/64389 | 11/2000 |
| WO | WO 2000/64390 | 11/2000 |
| WO | WO 2000/64391 | 11/2000 |
| WO | WO 2000/64393 | 11/2000 |
| WO | WO 2000/67687 | 11/2000 |
| WO | WO 2000/72788 | 12/2000 |
| WO | WO 2001/41685 | 6/2001 |
| WO | WO 2001/50943 | 7/2001 |
| WO | WO 2001/78656 | 10/2001 |
| WO | WO 2001/97727 | 12/2001 |
| WO | WO 2002/36052 | 5/2002 |
| WO | WO 2002/080811 | 10/2002 |
| WO | WO 2002/087418 | 11/2002 |
| WO | WO 2002/089699 | 11/2002 |
| WO | WO 2002/102274 | 12/2002 |
| WO | WO 2003/041622 | 5/2003 |
| WO | WO 2003/045290 | 6/2003 |
| WO | WO 2003/073968 | 9/2003 |
| WO | WO 2004/014218 | 2/2004 |
| WO | WO 2004/043231 | 5/2004 |
| WO | WO 2004/093761 | 11/2004 |
| WO | WO 2005/016418 | 2/2005 |
| WO | WO 2005/105197 | 11/2005 |
| WO | WO 2005/107664 | 11/2005 |
| WO | WO 2006/036715 | 4/2006 |
| WO | WO 2007/130393 | 11/2007 |
| WO | WO 2010/077987 | 7/2010 |
| WO | WO 2010/093945 | 8/2010 |
| WO | WO 2011/020633 | 2/2011 |

(56) References Cited

FOREIGN PATENT DOCUMENTS

| WO | WO 2013/040079 | 3/2013 |
| --- | --- | --- |
| WO | WO 2014/150292 | 9/2014 |
| WO | WO 2014/151070 | 9/2014 |
| WO | WO 2014/164569 | 10/2014 |
| WO | WO 2015/073571 | 5/2015 |
| WO | WO 2015/184173 | 12/2015 |
| WO | WO 2016/154066 | 9/2016 |
| WO | WO 2016/187355 | 11/2016 |
| WO | WO 2017/015633 | 1/2017 |
| WO | WO 2017/030917 | 2/2017 |
| WO | WO 2017/040853 | 3/2017 |
| WO | WO 2017/040855 | 3/2017 |
| WO | WO 2017/053885 | 3/2017 |
| WO | WO 2017/087713 | 5/2017 |
| WO | WO 2017/184881 | 10/2017 |
| WO | WO 2019/036025 | 2/2019 |
| WO | WO 2019/070385 | 4/2019 |
| WO | WO 2020/172615 | 8/2020 |

OTHER PUBLICATIONS

Bae, et al., "In vitro experiment of the pressure regulating valve for a glaucoma implant", Journal of Micromechanics and Microengineering 13.5, 13:613-619, No. 5, Sep. 2003.
Bucciarelli, Patrice D., "Working Model is Next Step in Team's Long Journey to Commercial Product", Healthfirst, Business First of Louisville, louisville.bizjournals.com, Feb. 27, 2004.
Cairns, J.E., "Trabeculectomy: Preliminary report of a new method", Am. J. Ophthalmology, 66:673-79 (1968).
"Changing Perspectives in Glaucoma Management," Innovations in Glaucoma 2010.
Chen, et al., "Trabeculetomy combined with implantation of sil-icon rubber slice for intractable glaucoma", Eye Science, 18:95-98, vol. 2, Jun. 2002.
Fine, Ben S., et al., "A Clinicopathologic Study of Four Cases of Primary Open-Angle Glaucoma Compared to Normal Eyes", American Journal of Ophthalmology, vol. 91, No. 1, 1981, pp. 88-105.
Fiore et al., "Use of neodymium: YAG laser to open an occluded molteno tube", Ophthalmic Surgery, May 1989; 20(5): 373-74.
Gimbel et al., "Small incision trabeculotomy combined with phacoemulsificatin and intraocular lens implantation", J Cataract Refract Surg, vol. 19:92-96 (Jan. 1993).
Gothwal et al., "Migration of seton into the anterior chamber", Eye, 16:85-97, 2002.
Grant, W.M., Md, "Further Studies on Facility of Flow Through the Trabecular Meshwork", AMA Archives of Ophthalmology, Oct. 1958, vol. 60, pp. 523-533.
Hoskins et al., "Diagnosis and Therapy of the Glaucomas", Chapter 4: Aqueous Humor Outflow, 61 Edition, pp. 41-66 (1989) (28 pages).
Huang et al., "Intermediate-term Clinical Experience with the Ahmed Glaucoma Valve Implant", 127 Am. J. Ophthalmol. 27 (Jan. 1999).
Hulzen et al., "Effect of Fixation on Juxtacanalicular Tissue and Schlemm's canal", Investigative Ophthalmology & Visual Science, vol. 37, No. 1 (Jan. 1996).
Johnson, et al. "Mechanisms and Routes of Aqueous Humor Drainage" in D.M. Albert, & F.A. Jakobiec (Eds.), Principles and Practice of Ophthalmology, pp. 2577-2595, WB Saunders, Philadelphia (2000).
Johnson et al., "Schlemm's Canal Becomes Smaller After Successful Filtration Surgery", (reprinted) ARCM Ophthalmol/vol. 118, Sep. 2000 (www.archophthalmol.com) p. 1251-1256.
Jordan et al., "A Novel Approach to Suprachoroidal Drainage for the Surgical Treatment of Intractable Glaucoma", J Glaucoma, vol. 15, No. 3, Jun. 2006, pp. 200-205.
Kampik et al. "Nutzen und Risiken Augenärzticher Therapie", Hauptreferate der XXXIII, Essener Fortbildung für Augenärzte, Dec. 1998. (English translated version enclosed Benefits and Risks of Ophthalmological Therapy).

Kershner, "Nonpenetrating trabulectomy with placement of a collagen drainage device", J. Cataract Refract. Sug., 21:608-611 (1995).
Klemm et al., "Experimental use of space-retaining substances with extended duration: functional and morphological results", Graefe's Arch Clin Exp Ophthalmol (1995) 233:592-597.
Krupin et al., "Filtering valve implant surgery for eyes with neovascular glaucoma", 89 Am. J. Ophthalmol. 338 (Mar. 1980).
Mermoud et al., "Comparison of deep sclerectomy with collagen implant and trabeculectomy in open- angle glaucoma", J. Cataract Refract. Surg., vol. 25, No. 3, Mar. 1999, pp. 323-331 (abstract only).
Miyazaki et al., "Postoperative Results of Combined Trabeculotomy, Phacoemulsification and Intraocular Lens Implantation With Self-Sealing Wound", Japanese Journal of Ophthalmic Surgery, 1997, pp. 537-542, vol. 10, No. 4.
Molteno et al., "Implants for draining neovascular glaucoma", 61 Br. J. Ophthalmol. 120 (1977).
Moses, Robert A., M.D.; "Circumferential Flow in Schlemm's Canal", American Journal of Ophthalmology, Sep. 1979, vol. 88, No. 3, Part II, :pp. 585-591.
Nguyen et al., "Complications of Baerveldt Glaucoma Drainage Implants", 116 Arch. Ophthalmol. 571 (May 1998).
Refojo, "Current status of biomaterials in ophthalmology", Survey of ophthalmology, 26:257-265, No. 5, 1982.
Rizq, et al., "Intraocular Pressure measurement at the Chroid Surface: A Feasibility Study with Implications for Implantable Microsystems", Br J Ophthalmol 2001; 85:868-871, Jul. 2001.
Sampaolesi, et al., "Scanning Electron Microscopy of the Trabecular Meshwork in Normal-Glaucomatous Eyes", Invest Ophthalmol Vis Sci, pp. 302-314 (1977).
Saxena, Sandeep. "Clinical Ophthalmology". 2011. pp. 245.
Schocket, "Investigations of the Reasons for Success and Failure in the Anterior Shunt-to-the Encircling-Band Procedure in the Treatment of Refractory Glaucoma", Tr. Am. Ophth. Soc., 84:743 (1986).
Scott, et al., "Use of glaucoma drainage devices in the management of glaucoma associated with aniridia", American Journal of Ophthalmology, 135:155-159, No. 2, Feb. 1, 2003.
Shields, M. Bruce, Md, "A Study Guide for Glaucoma: Aqueous Humor Dynamics", Copyright 1982, pp. 6-43.
Spiegel, Detlev, "Benefits and Risks of Ophthalmological Treatment" Bucherel des Augenarztes | The Ophthalmologist's Library, vol. 139, Oct. 15, 1998.
Spiegel, "7 chirurgische Glaukomtherapie", pp. 79-88 (English translation enclosed).
Spiegel et al., "Schlemm's Canal Implant: A New Method to Lower Intraocular Pressure in Patients With POAG", Opthalmic Surgery and Lasers, vol. 30(6):492-494 (1999).
Stefansson, J., "An Operation for Glaucoma", American J. Ophthalmology, 8:681-693 (1925).
Tham, et al., "Incisional surgery for angle closure glaucoma", Seminars in Ophthalmology, 17:92-99, No. 2, Jun. 2002.
Topouzis et al., "Follow-up of the Original Cohort With the Ahmed Glaucoma Valve Implant", 128 Am. J. Ophthalmol. 198 (Aug. 1999).
"Transcend Medical CyPass® System—Instructions for Use," (Release date Apr. 29, 2013).
Tripathi et al., "Functional Anatomy of the Anterior Chamber Angle", Biomedical Foundation of Ophthalmology, vol. 1, Chapter 10,pp. 1-74; edited by Thomas Dune and Edward Jaeger, Revised Edition, 1983,—Harper & Row, Publishers.
Tun et al., "Assessment of Trabecular Meshwork Width Using Swept Source Optical Coherence Tomography", 251:6 Graefes Arch. Clin. Exp. Ophthalmol. 1587 (2013).
Wagner, et al., "Characterization of Uveoscleral Outflow in Enucleated Porcine Eyes Perfused Under Constant Pressure", Invest Ophthalmol Vis Sci. Sep. 2004: 45(9): 3203-3206 (9 pages).
Webster's Third New International Dictionary of the English Language (Unabridged), definitions of "deploy" and "deployment", p. 605 (2002) (4 pages).
Wilcox et al. "Hypothesis for Improving Accessory Filtration by Using Geometry", J. Glaucoma, vol. 3, No. 3, pp. 244-247 (1994).
Wilcox et al., Latest Research: Tear Biomarkers, Jun. 29, 2011, 5 pages.

(56) References Cited

OTHER PUBLICATIONS

Wilcox et al. "Performance of a New, Low-volume High-Surface Area Aqueous Shunt in Normal Rabbit Eyes", J. Glaucoma, vol. 9, No. 1, pp. 74-82 (Feb. 2000).
Wilson, Ellen D., "Implants offer choices for glaucoma surgeons", EW Glaucoma, Oct. 11, 1999, website "http:-www.eyeorld.org-sep99-999p60.asp".
Yan et al., "Schlemm's Canal and Trabecular Meshworkin Eyes with Primary Open Angle Glaucoma: A Comparative Study Using High-Frequency", PLOS ONE, 15 pages, Jan. 4, 2016.
Office Action dated Oct. 4, 2005 (Restriction Requirement) in U.S. Appl. No. 10/634,213, filed Aug. 5, 2003, entitled Devices and Methods for Treatment of Ocular Disorders.
Office Action dated Jan. 19, 2006 in U.S. Appl. No. 10/634,213, filed Aug. 5, 2003, entitled Devices and Methods for Treatment of Ocular Disorders.
Office Action (Final) dated Oct. 2, 2006 in U.S. Appl. No. 10/634,213, filed Aug. 5, 2003, entitled Devices and Methods for Treatment of Ocular Disorders.
Office Action dated June 25, 2007 in U.S. Appl. No. 10/634,213, filed August 5, 2003, entitled Devices and Methods for Treatment of Ocular Disorders.
Office Action dated Mar. 23, 2010 in U.S. Appl. No. 11/836,106, filed Aug. 8, 2007, entitled Devices and Methods for Treatment of Ocular Disorders.
Office Action dated Apr. 4, 2008 in U.S. Appl. No. 10/634,213, filed Aug. 5, 2003, entitled Devices and Methods for Treatment of Ocular Disorders.
Office Action dated May 13, 2009 in U.S. Appl. No. 10/634,213, filed Aug. 5, 2003, entitled Devices and Methods for Treatment of Ocular Disorders.
Office Action (Final) dated December 28, 2009 in U.S. Appl. No. 10/634,213, filed Aug. 5, 2003, entitled Devices and Methods for Treatment of Ocular Disorders.
Office Action (Interview Summary) dated Mar. 11, 2010 in U.S. Appl. No. 10/634,213, filed Aug. 5, 2003, entitled Devices and Methods for Treatment of Ocular Disorders.
Supplementary European Search Report in related European application No. 04779911.9, dated Jul. 18, 2007, 3 pp.
Office Action in related European application No. 04779911.9, dated Apr. 17, 2009, 4 pp.
Office Action in corresponding EP Application No. 04779911.9 mailed Sep. 30, 2010, 4 pp.
European Exam Report, EPO App. No. 08 102 896.1, dated Nov. 4, 2010.
Communication from European Patent Office for European App. No. 08102896.1 (Jul. 2, 2012) (5 pages).
International Search Report and Written Opinion in PCT/US2016/053570 mailed Mar. 9, 2017.
Appeal in European Application No. 08102896.1 dated Aug. 27, 2012.
International Preliminary Report on Patentability in PCT/US2016/053570 dated Mar. 27, 2018.

METHOD FOR CONTROLLING PLACEMENT OF INTRAOCULAR IMPLANTS

CROSS-REFERENCE TO RELATED APPLICATIONS

This application is a divisional application of U.S. application Ser. No. 16/146,786, filed Sep. 28, 2018, which claims priority to U.S. Provisional Application No. 62/564,972 filed Sep. 28, 2017, the entire contents of each of which are hereby incorporated by reference herein.

FIELD OF THE INVENTION

This disclosure generally relates to intraocular implants and the placement thereof within the eye, and relates more particularly to an apparatus and method for identifying locations of collector ducts, or channels, of the eye and positioning intraocular implants near the identified locations.

BACKGROUND

A human eye is a specialized sensory organ capable of light reception and is able to receive visual images. Aqueous humor is a transparent liquid that fills at least the region between the cornea, at the front of the eye, and the lens. A trabecular meshwork, located in an anterior chamber angle, which is formed between the iris and the cornea, normally serves as a drainage channel for aqueous humor from the anterior chamber so as to maintain a balanced pressure within the anterior chamber of the eye.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork normally allows the aqueous humor to enter Schlemm's canal, which then empties into aqueous collector channels in the posterior wall of Schlemm's canal and then into aqueous veins, which form the episcleral venous system. Aqueous is continuously secreted by a ciliary body around the lens, so there is a constant flow of aqueous from the ciliary body to the anterior chamber of the eye. Pressure within the eye is determined by a balance between the production of aqueous and its exit through the trabecular meshwork (major route) and uveoscleral outflow (minor route). The portion of the trabecular meshwork adjacent to Schlemm's canal (the juxtacanilicular meshwork) causes most of the resistance to aqueous outflow.

Glaucoma is broadly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous from the anterior chamber of the eye. Open-angle glaucoma is any glaucoma in which the exit of aqueous through the trabecular meshwork is diminished while the angle of the anterior chamber remains open. For most cases of open-angle glaucoma, the exact cause of diminished filtration is unknown. Primary open-angle glaucoma is the most common of the glaucomas, and is often asymptomatic in the early to moderately advanced stages of glaucoma. Patients may suffer substantial, irreversible vision loss prior to diagnosis and treatment. However, there are secondary open-angle glaucomas that may include edema or swelling of the trabecular spaces (e.g., from corticosteroid use), abnormal pigment dispersion, or diseases such as hyperthyroidism that produce vascular congestion.

Because the trabecular meshwork and juxtacanilicular tissue together provide the majority of resistance to the outflow of aqueous, they are logical targets for surgical removal in the treatment of open-angle glaucoma. In addition, minimal amounts of tissue need be altered and existing physiologic outflow pathways can be utilized. Some procedures bypass the trabecular meshwork and juxtacanilicular tissue to drain fluid to physiologic outflow channels.

SUMMARY

In accordance with some embodiments, a method of positioning intraocular implants at or near collector ducts of Schlemm's canal. The method comprises positioning a handheld peristaltic rotor device on a corneal surface of an eye, the handheld peristaltic rotor device comprising a rotor having a plurality of compression elements; rotating the rotor such that the plurality of compression elements create a peristaltic movement of blood from one or more occluded episcleral veins to Schlemm's canal; identifying a location of at least one collector duct, or channel, of the eye based on the refluxed blood within Schlemm's canal; delivering an implant through an incision (e.g., corneal incision or incision through a limbus) in the eye; and placing an implant within the eye such that the implant is located at or near the identified location of the at least one collector duct. The implant may drain aqueous from an anterior chamber of the eye to Schlemm's canal and bypass the trabecular meshwork.

In accordance with some embodiments, a method of identifying a location of one or more collector ducts of Schlemm's canal of an eye is disclosed. The method comprises positioning a handheld peristaltic rotor device on a surface of an eye, the handheld rotor device comprising a rotor having a compression element; rotating the rotor such that the compression element of the rotor induces a peristaltic movement of blood into Schlemm's canal from one or more occluded episcleral veins, and identifying a location of at least one collector duct of the eye based at least in part on the refluxed blood. In some embodiments, rotating the rotor comprises manual rotation (partial revolution rotation or multiple turn or revelation rotation). The rotation may be effected by a handle or level coupled to the rotor or by directly rotating the rotor with the fingers. In some embodiments, rotating the rotor comprises winding an internal spring by manually rotating the rotor in a first (e.g., clockwise) direction and then releasing the rotor to cause the spring to unwind and the rotor to rotate in an opposite (e.g., counter-clockwise) direction.

A handheld peristaltic rotor device for locating collector ducts of Schlemm's canal of an eye is also disclosed. The handheld peristaltic rotor device comprises a rotor having a proximal portion and a distal open end, the distal open end comprising a distal rim surface and a corneal clearance portion; and a plurality of compression elements protruding from the distal rim surface, wherein the rotor and the plurality of compression elements are configured to cause a blood reflux into Schlemm's canal from one or more occluded episcleral surface region of an eye by positioning the rotor on the episcleral surface of the eye and rotating the rotor. The handheld peristaltic rotor device may also comprise an optical element that remains stationary while the rotor is rotated either by hand or a wound spring. The device may comprise a handle connected to the proximal portion of the rotor to facilitate manual rotation of the rotor. In some embodiments, a spring is included having a first end coupled to the optical portion and a second end coupled to the proximal portion of the rotor, wherein the spring is configured to cause rotation of the rotor. The plurality of compression elements may comprise ribs or fins that taper in height along their length so as to induce the peristaltic effect. The lengths of the compression elements may overlap. The plurality of compression elements may be formed of a compliant polymeric material so as to deform when in contact with an eye surface. The optical element or portion may include a magnifying lens (e.g., gonio lens) to facilitate visualization of reflux. The optical element or portion may be detachably coupled to the proximal portion of the rotor if the rotor is intended for single use or for sterilization.

DETAILED DESCRIPTION

Figure 1:
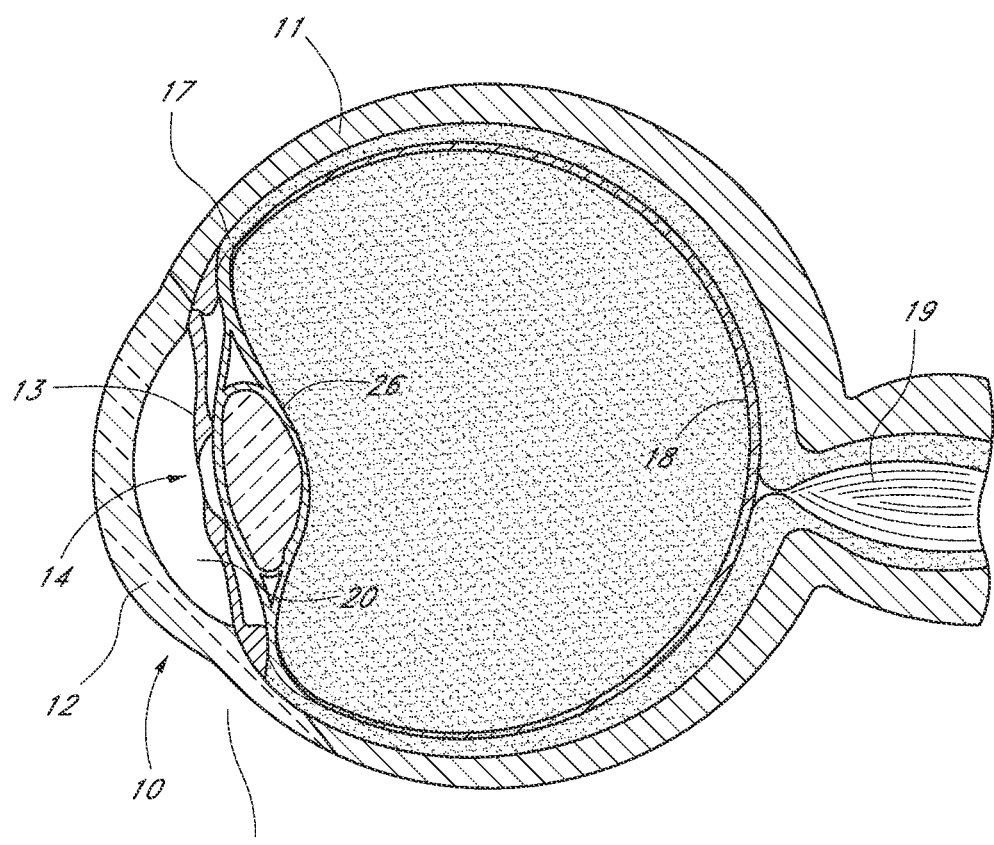
FIG. 1 is a sectional view of an overall anatomy of an eye.

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may comprise several novel features, no single one of which is solely responsible for its desirable attributes or which is essential to practicing the inventions herein described.

In some circumstances, an intraocular implant (e.g., a shunt, stent or the like) can be implanted into the trabecular meshwork of the eye of a patient suffering from an ocular disorder, such as glaucoma, so as to create a fluid passageway between the anterior chamber and Schlemm's canal behind the trabecular meshwork in the patient's eye. The fluid passageway allows aqueous fluid to flow from the anterior chamber of the eye through the fluid passageway (e.g., bypass) created by the implant, into Schlemm's canal, and out of the patient's eye through the episcleral venous pathways, thereby relieving the elevated intraocular pressure associated with glaucoma. In some embodiments, the devices and methods described herein can used to facilitate reduction of intraocular pressure in pigmentary glaucoma patients and/or pseudoexfoliation glaucoma patients.

Pressure within the eye is determined by a balance between the production of aqueous fluid and its exit through the canalicular outflow (e.g., through the trabecular meshwork) and uveoscleral outflow routes or pathways. The portion of the trabecular meshwork adjacent to Schlemm's canal (the juxtacanilicular meshwork) is believed to cause most of the resistance to aqueous fluid outflow. Accordingly, it can be advantageous to insert ocular implants, such as shunts or stents, to promote and maintain an increased level of aqueous fluid flow out of Schlemm's canal through the trabecular meshwork.

Schlemm's canal contains numerous outflow channels known as collector ducts, or collector channels. In some circumstances, it can be desirable to place an implant at a position in the trabecular meshwork that is near (e.g., within 1 mm of) one of the collector ducts, or channels, so as to provide an effective fluid passageway between the anterior chamber and Schlemm's canal. The various collector ducts of Schlemm's canal can vary in size, and it can be desirable to position an outlet of the implant near (e.g., within 1 mm of) a large collector duct so as to allow a sufficient amount of fluid to drain out of the anterior chamber of the eye to relieve the elevated intraocular pressure in a more efficient manner.

The implant can be implanted into the trabecular meshwork using a surgical procedure in which the implant is placed in or on a delivery device and inserted through an incision, including a self-sealing incision, in the cornea, limbus, or the adjacent scleral or conjunctival tissue, then transported across the anterior chamber (e.g., in an ab interno manner), and implanted into the trabecular meshwork on the side of the eye substantially across from the incision. In other embodiments, the implant can be implanted on the same side of the eye as the incision (e.g., corneal incision). In some embodiments, the surgical procedure is performed using a surgical microscope positioned over the patient's eye and a gonioprism is used to allow the ophthalmologist or other clinician to see into the anterior chamber of the eye as the implant is implanted. Although the trabecular meshwork can be viewed using this system, the locations of collector ducts of Schlemm's canal are not readily visible because they are hidden behind the trabecular meshwork. Therefore, the ophthalmologist or other clinician may be unable to target a specific collector duct, or channel, when placing the implant. Placement of the implants is sometimes guided by rules of thumb or general guidelines such as placing the implant in the nasal inferior quadrant of the trabecular meshwork, where the collector ducts are believed to be more prevalent. However, because the ophthalmologist may be unable to identify the actual locations of the collector ducts in the eye, the successful placement of the implant near a collector duct, including large collector ducts, can ultimately rely on a degree of chance without use of embodiments of the inventions described herein.

Anatomy

Figure 2:
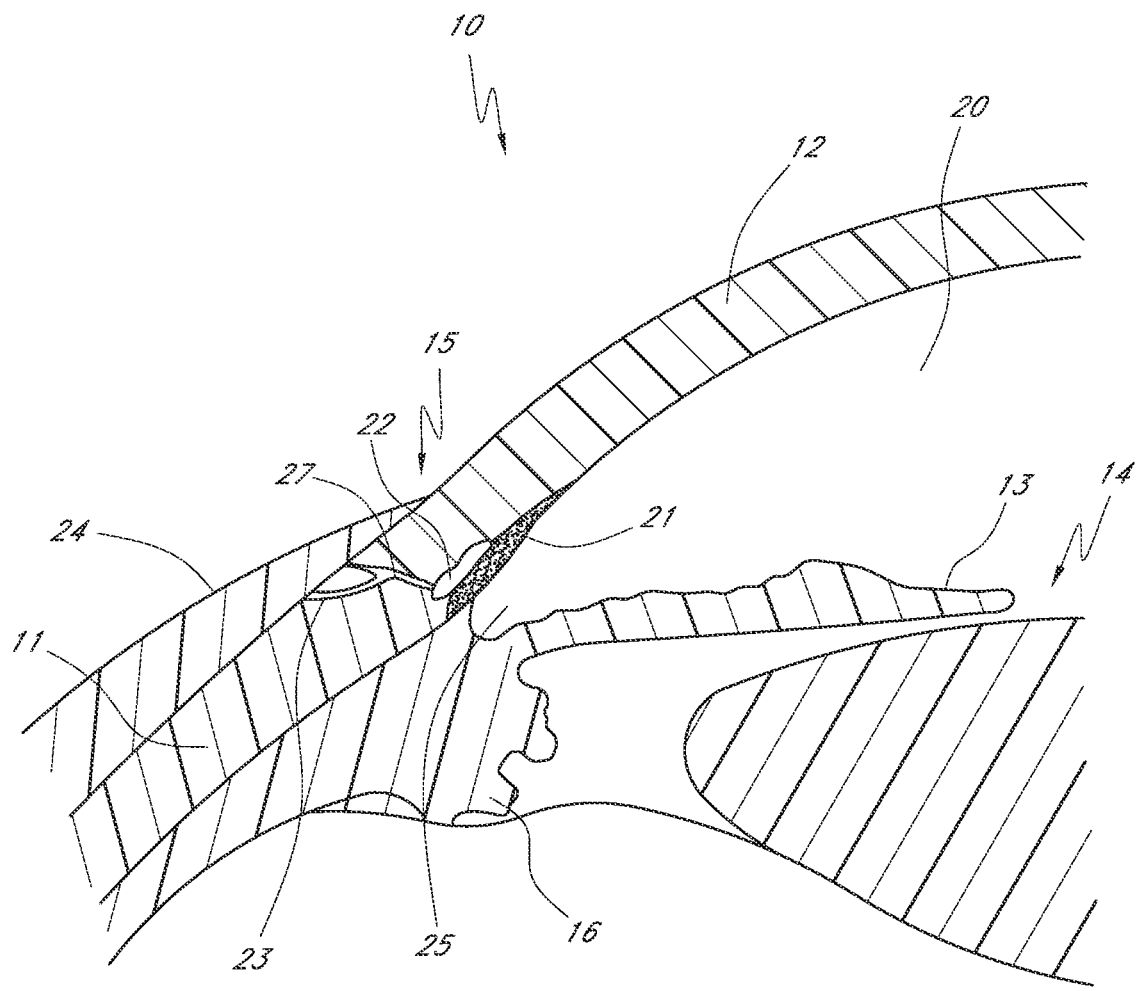
FIG. 2 is a close-up sectional view of an anterior chamber angle of the eye of FIG. 1.

FIG. 1 shows a sectional view of an eye 10, while FIG. 2 shows a close-up view, showing the relative anatomical locations of the trabecular meshwork, the anterior chamber, and Schlemm's canal within the eye 10. Thick collagenous tissue known as the sclera 11 covers the entire eye 10 except that portion covered by the cornea 12. The cornea 12 is a thin transparent tissue that focuses and transmits light into the eye and the pupil 14 which is the circular hole in the center of the iris 13 (colored portion of the eye). The cornea 12 merges into the sclera 11 at a juncture referred to as the limbus 15. The ciliary body 16 begins internally in the eye and extends along the interior of the sclera 11 and becomes the choroid 17. The choroid 17 is a vascular layer of the eye underlying retina 18. The optic nerve 19 transmits visual information to the brain and is sequentially destroyed by glaucoma.

The anterior chamber 20 of the eye 10, which is bound anteriorly by the cornea 12 and posteriorly by the iris 13 and the lens 26, is filled with aqueous fluid. Aqueous humor (also referred to as "aqueous") is produced primarily by the ciliary body 16 and reaches the anterior chamber angle 25 formed between the iris 13 and the cornea 12 through the pupil 14. In a normal eye, the aqueous is removed through the trabecular meshwork 21. The aqueous passes through the trabecular meshwork 21 into Schlemm's canal 22 and through collector ducts or channels 27, which merge with blood-carrying episcleral veins and into venous circulation. Intraocular pressure of the eye 10 is maintained by the intricate balance of secretion and outflow of the aqueous in the manner described above. Glaucoma is characterized by the excessive buildup of aqueous fluid in the anterior chamber 20 which produces an increase in intraocular pressure (fluids are relatively incompressible and pressure is directed equally to all areas of the eye).

Blood Reflux

Figure 3A:
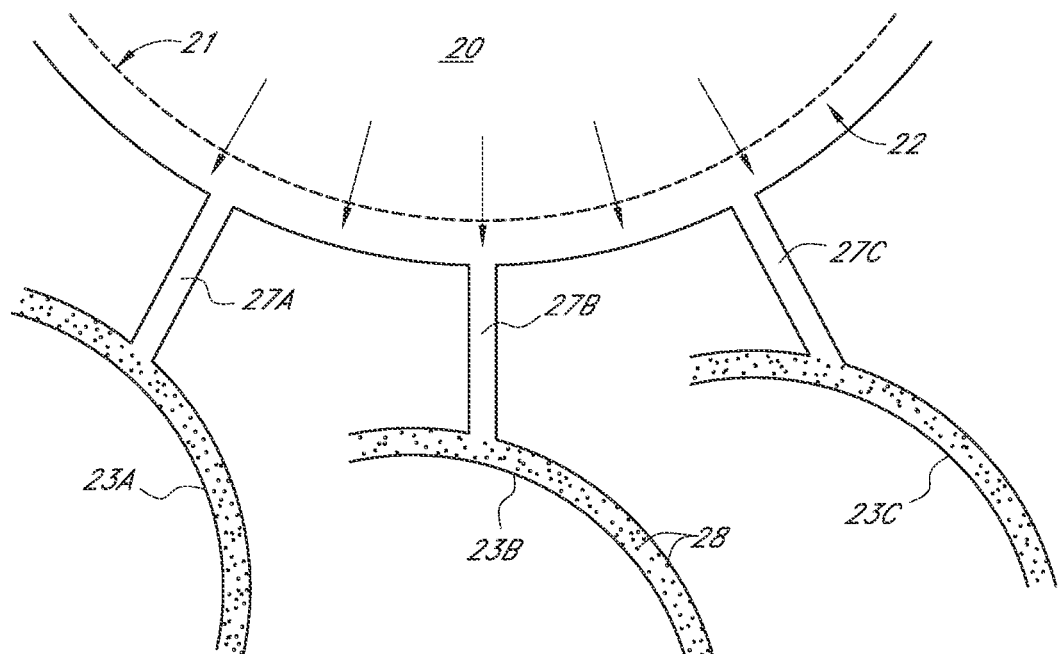
FIG. 3A illustrates a diagram of normal aqueous fluid outflow.

With reference to FIG. 3A, aqueous normally flows from the anterior chamber 20 through the fenestrated trabecular meshwork 21 and into Schlemm's canal 22. The aqueous then empties into the aqueous collector ducts, or channels 27 in the posterior wall of Schlemm's canal 22 and then into the blood-carrying episcleral veins 23, which form the episcleral venous system. The aqueous fluid mixes with, and dilutes, the blood in the episcleral veins. The dotted areas indicate blood 28. Aqueous is continuously secreted by a ciliary body around the lens 26, so there is a constant flow of the aqueous from the ciliary body to the anterior chamber 20 of the eye 10. Accordingly, in normal eyes, there is normally minimal to no blood flow within Schlemm's canal 22, as illustrated by the absence of blood (as evidenced by a concentration of red blood cells sufficiently high to be visible to a clinician) within Schlemm's canal 22 in FIG. 3A, thereby making it difficult to observe Schlemm's canal.

Figure 3B:
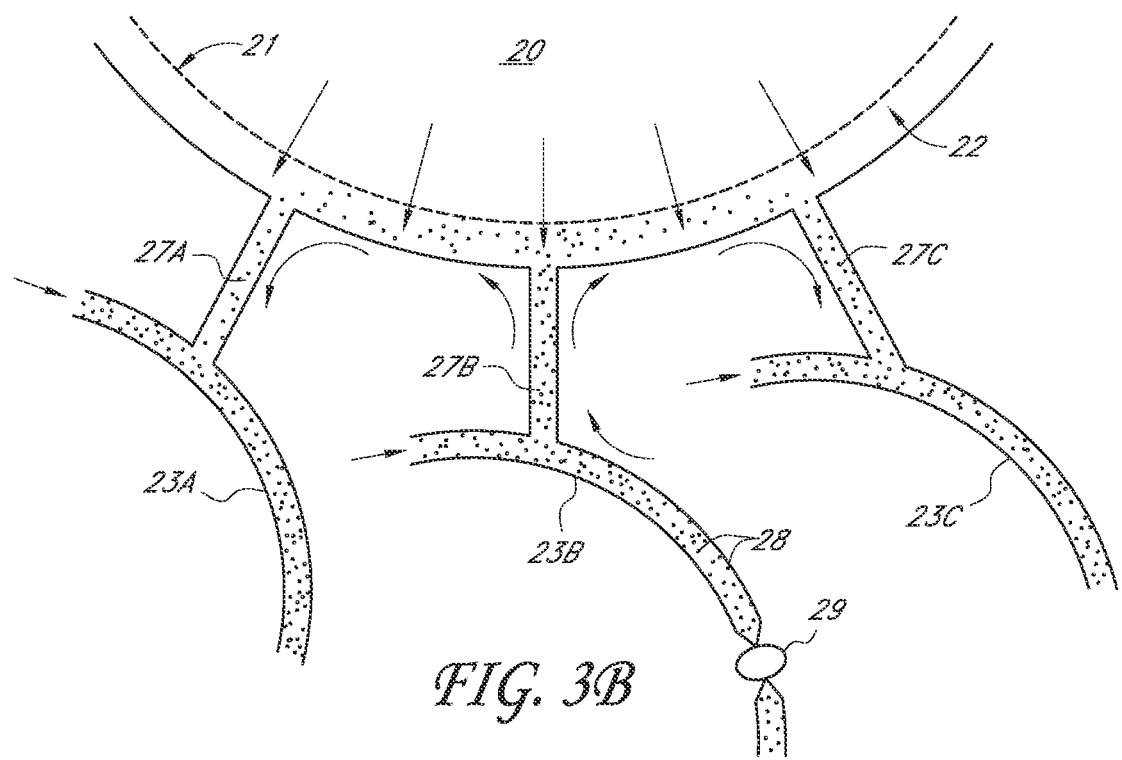
FIG. 3B illustrates a diagram of blood reflux into Schlemm's canal caused by occlusion of at least one episcleral vein.

With reference to FIG. 3B, blood 28 can be refluxed into Schlemm's canal 22 by occlusion of one or more episcleral veins 23 of the episcleral venous system. For example, if episcleral vein 23B is occluded, the blood pressure rises upstream from the occlusion 29 until blood 28 refluxes into the collector duct 27B and eventually into Schlemm's canal 22. Because of the circumferential flow within Schlemm's canal 22, the blood follows a path of least resistance along Schlemm's canal 22 to another collector duct 27A, 27C, whose episcleral vein is not occluded. As the blood flows within Schlemm's canal 22, the blood is diluted by the aqueous within Schlemm's canal 22. Accordingly, the highest concentration of blood and blood particles within Schlemm's canal 22 is located at or near the inlet to the collector duct 27B. The region of Schlemm's canal adjacent the inlet to the collector duct 27B upstream of the occluded vein 23B, can take on a pinkish color due to the increased concentration of blood (made visible by red blood cells) 28 within the region. The location of the collector duct 27B can thus be identified by observing the pinkish region through a gonioscope. The identified location can then be used to more precisely place an implant near a collector duct, or channel, 27 of Schlemm's canal 22, thereby increasing aqueous outflow and reducing intraocular pressure.

Peristaltic Rotor

Figure 4A:
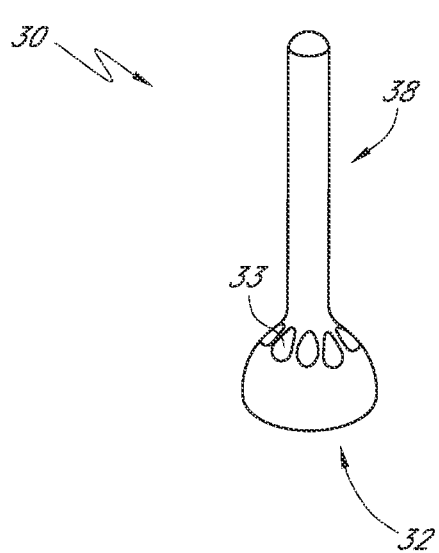
FIGS. 4A-4B illustrate an embodiment of a handheld peristaltic rotor device for generating blood reflux into Schlemm's canal.
Figure 4B:
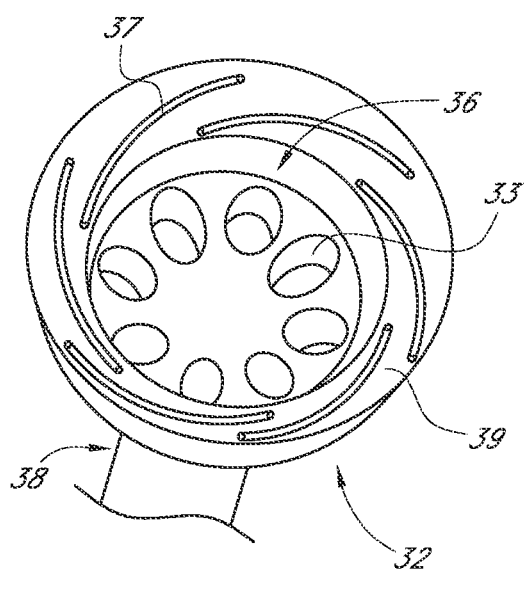

FIGS. 4A-4I illustrate various embodiments of a blood reflux generation and/or identification device 30. The blood reflux generation and/or identification device 30 may comprise a handheld peristaltic rotor device for generating blood reflux within Schlemm's canal 22 positioned on a corneal surface of the eye. The handheld peristaltic rotor device 30 can include a handle 38 attached to a rotor member or portion 32. The handle 38 can be an elongated rod made of a substantially rigid material, such as, for example, a polyvinyl chloride (PVC) rod. The handle 38 may be coupled to the rotor member 32 at any suitable location and can extend outward from the rotor member 32 to facilitate rotation of the rotor member 32. The rotor member 32 can be generally cup-shaped, having a distal open end and a proximal end. The distal open end can include a distal rim surface 39 and a corneal clearance portion 36. The proximal end of the rotor member 32 can be connected to the handle 38. The rotor member 32 can include a plurality of anti-suction vents 33 allowing passage of air from the corneal clearance portion 36 to an external surface of the rotor member 32. In some embodiments, the anti-suction vents 33 can be oval-shaped holes circumferentially spaced from the center of the rotor member 32, as best shown in FIGS. 4A and 4B. The holes may have other shapes in other embodiments (e.g., circle, ellipse, oblong shape).

The height of the cup-shaped rotor member 32 can be between about 7 mm to about 20 mm (e.g., 7 mm-10 mm, 10 mm-15 mm, 15 mm-20 mm, 7 mm-15 mm, 10 mm-20 mm, overlapping ranges thereof, or any value within the recited ranges). The diameter of the rotor member 32 can be between about 10 mm to about 25 mm (e.g., 10 mm-20 mm, 10 mm-15 mm, 15 mm-25 mm, 15 mm-20 mm, overlapping ranges thereof, or any value within the recited ranges). Heights and diameters outside these ranges are also possible. The distal rim surface 39 of the rotor member 32 can have an O-ring or a toroidal shape surrounding the corneal clearance portion 36. The distal rim surface 39 of the rotor member 32 can be configured to substantially conform to the contour of the episcleral surface region of the eye. The distal rim surface 39 can have a thickness configured to allow the rotor member 32 to concentrically rotate about the cornea 12. For example, the distal rim surface 39 can have a thickness of about 0.5 mm to about 10 mm (e.g., 0.5 mm-5 mm, 1 mm-5 mm, 0.5 mm-1.5 mm, 0.5 mm to 2 mm, 5 mm to 10 mm, overlapping ranges thereof, or any value within the recited ranges). A fluid or a gel can optionally be applied to the distal rim surface 39 of the rotor member 32.

The corneal clearance portion 36 can have a generally spherical-cap shape or other shape that can conform to the shape of the cornea 12 of an average human eye (e.g., adult or child eye). The height and the diameter of the corneal clearance portion 36 are similar to, or greater than, the height and the diameter size of the cornea 12. The height and the diameter of the corneal clearance portion 36 can allow the distal rim surface 39 of the peristaltic rotor device 30 to rotate about the cornea, without any part of the peristaltic rotor device 30 contacting the cornea. For example, the corneal clearance portion 36 can have a diameter of between about 9 mm and 12 mm. The height of the corneal clearance portion 36 can be between about 0.5 mm to about 3 mm (e.g., between 0.5 and 1.5 mm, between 0.5 mm and 2 mm, between 1 mm and 3 mm, overlapping ranges thereof, or any value within the recited ranges). Diameters and heights outside these ranges are also possible.

Figure 4C:
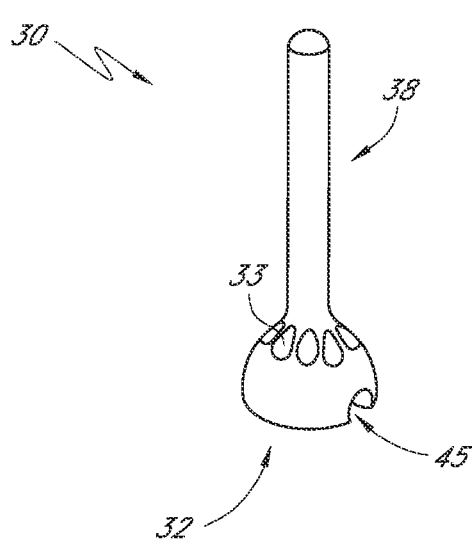
FIGS. 4C-4D illustrate an embodiment of a handheld peristaltic rotor device having an undercut.
Figure 4D:
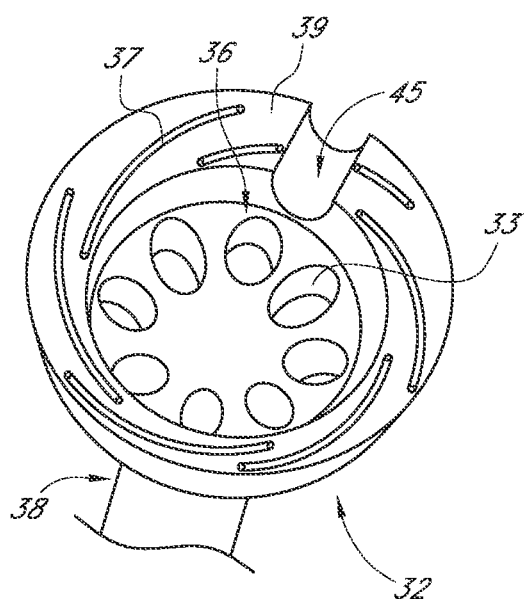
Figure 4E:
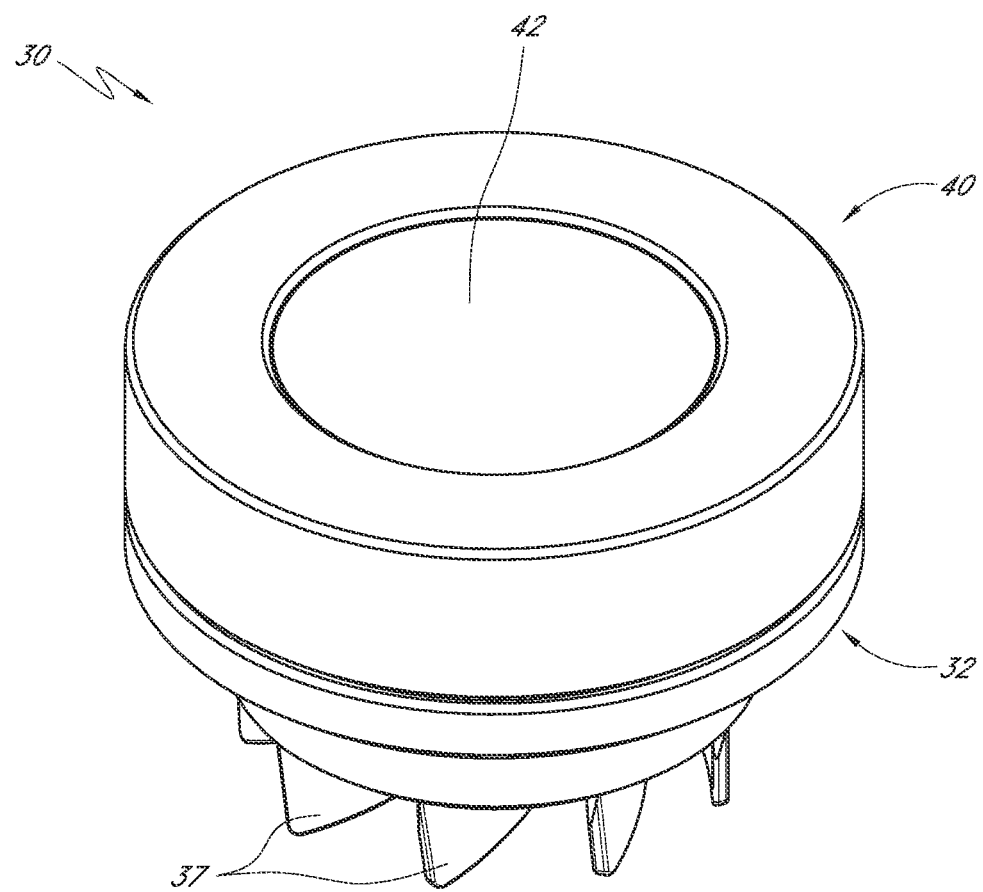
FIGS. 4E-4I illustrate a top perspective view, a side view, a bottom perspective view, a bottom view and a side cross-section view, respectively, of an embodiment of a handheld peristaltic rotor device.
Figure 4F:
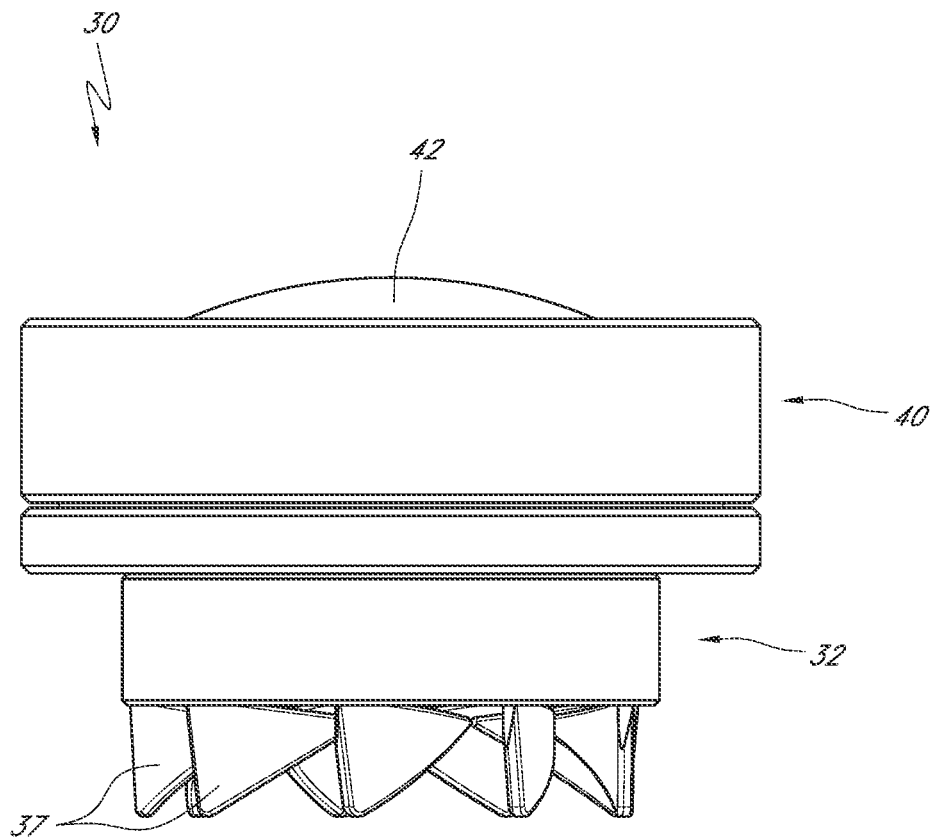
Figure 4G:
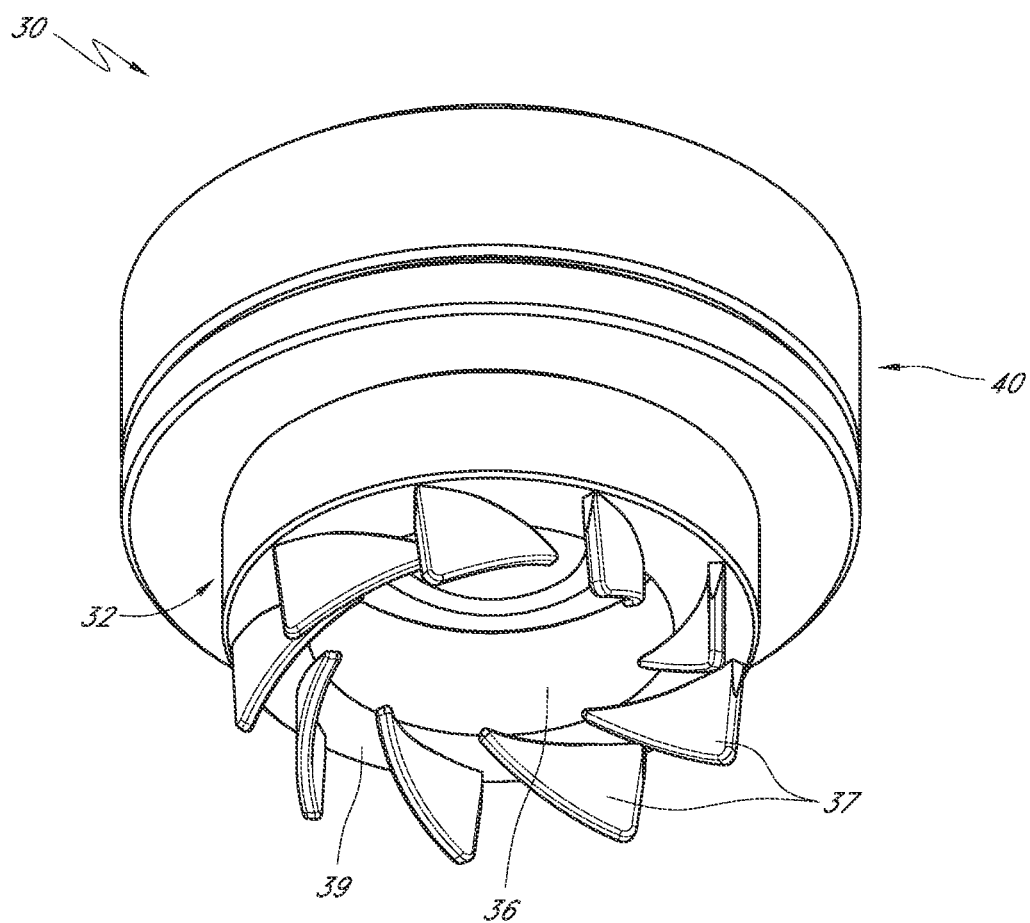
Figure 4H:
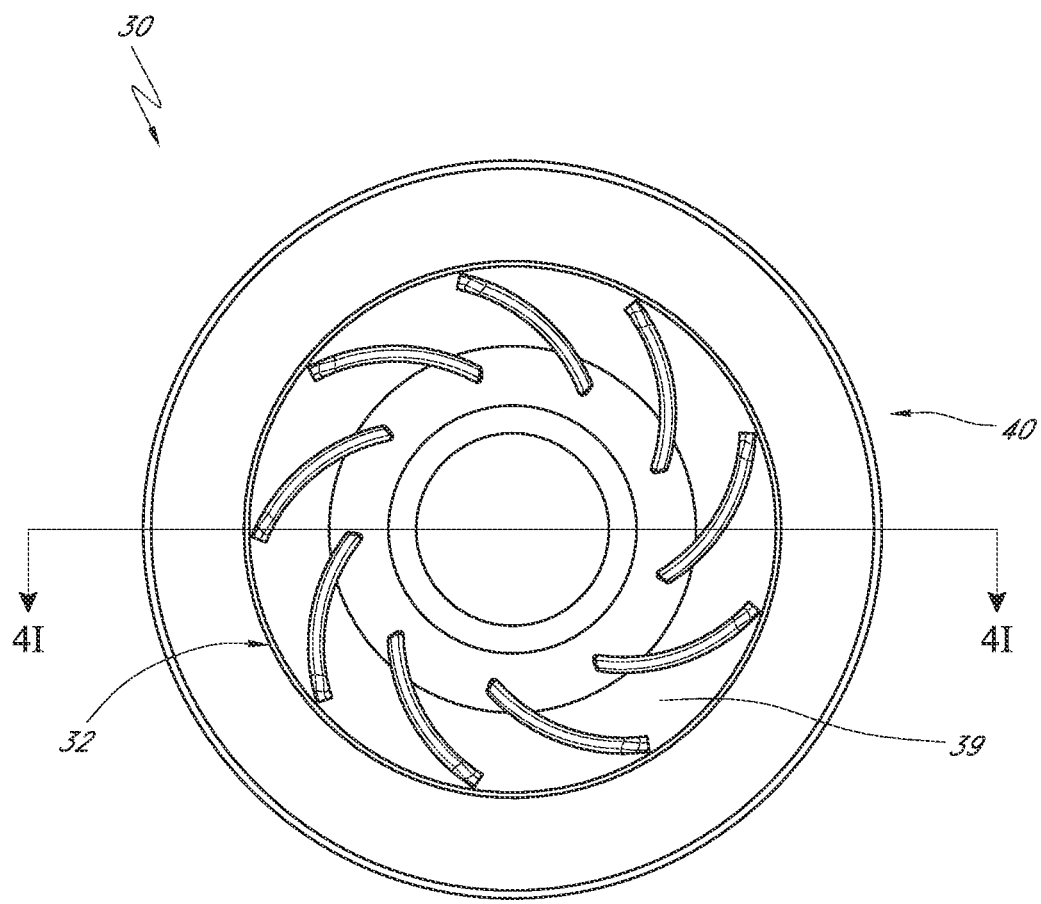

The structure of the rotor member 32 can also include an undercut 45, as shown in FIGS. 4C and 4D. The undercut can be used, for example, to increase the accessibility and introduction of devices to the eye, including the cornea, the limbus, or the adjacent scleral or conjunctival tissue of the eye. The undercut 45 can be configured to allow introduction of an elongate tip or a cannula portion 55 of an implant delivery instrument or other surgical instrument, as described in further detail below.

In some embodiments, the rotor member 32 can include two or more undercuts 45 radially spaced apart from each other. In such embodiments, a clinician may use the rotor 32 having two or more undercuts 45 to place a second implant within the eye such that the second implant is located at or near the identified location of a second collector duct. The rotor 32 having two or more undercuts 45 can also be used to determine a desired degree of rotation of the rotor member 32 about the cornea.

All or part of the rotor member 32 can be made of a substantially transparent material (e.g., glass, plastic, silicone, or other materials) so that light reflected from the subject's eye can be received by the distal rim surface 39, propagate through the transparent material, and be emitted by the proximal surface. In some embodiments, the handheld peristaltic rotor device 30 can include a plurality of optical elements configured to refract light reflected by the patient's ocular structure. In some embodiments, an opaque material, such as an opaque plastic can be used for the rotor member 32.

In some embodiments, the rotor member 32 can be formed of a flexible material (e.g., a soft polymer such as silicone) so as to enhance the conformability of the rotor member 32 with the surface of the eye. In other embodiments, the rotor member 32 can be constructed of a rigid or semi-rigid material. In some embodiments, the handle 38 can be made of a rigid or semi-rigid material. In other embodiments, the handle 38 can be made of a flexible material.

With reference to FIGS. 4E-4I, some embodiments of a blood reflux generation device (e.g., handheld peristaltic rotor device) 30 may not include the handle 38. The elements labeled with like numbers as FIGS. 4A-4D may include the same structural and functional features described above. The illustrated embodiment of the device 30 shown in FIGS. 4E-4I shows that the device 30 may include an optical element or portion 40 that can be coupled (permanently or removably) to the rotor member or portion 32. For example, the optical element or portion 40 may be coupled to the rotor member 32 with set screws or other fixation members (not shown) to couple the optical element 40 and the rotor member 32. The set screws or other fixation members may be positioned at various (e.g., 2, 3, 4) spaced-apart locations around a circumference of the optical element 40. The rotor member 32 may be configured for one-time use and be disposable. Accordingly, it may be advantageous to have the optical element or portion 40 be detachable from the rotor member 32 so that that the rotor member or portion 32 can be discarded and the optical element or portion 40 can be re-used. In some embodiments, the rotor member or portion 32 and/or the optical element or portion 40 can be sterilized and re-used. In some embodiments, the entire device 30 may be disposable.

Figure 4I:
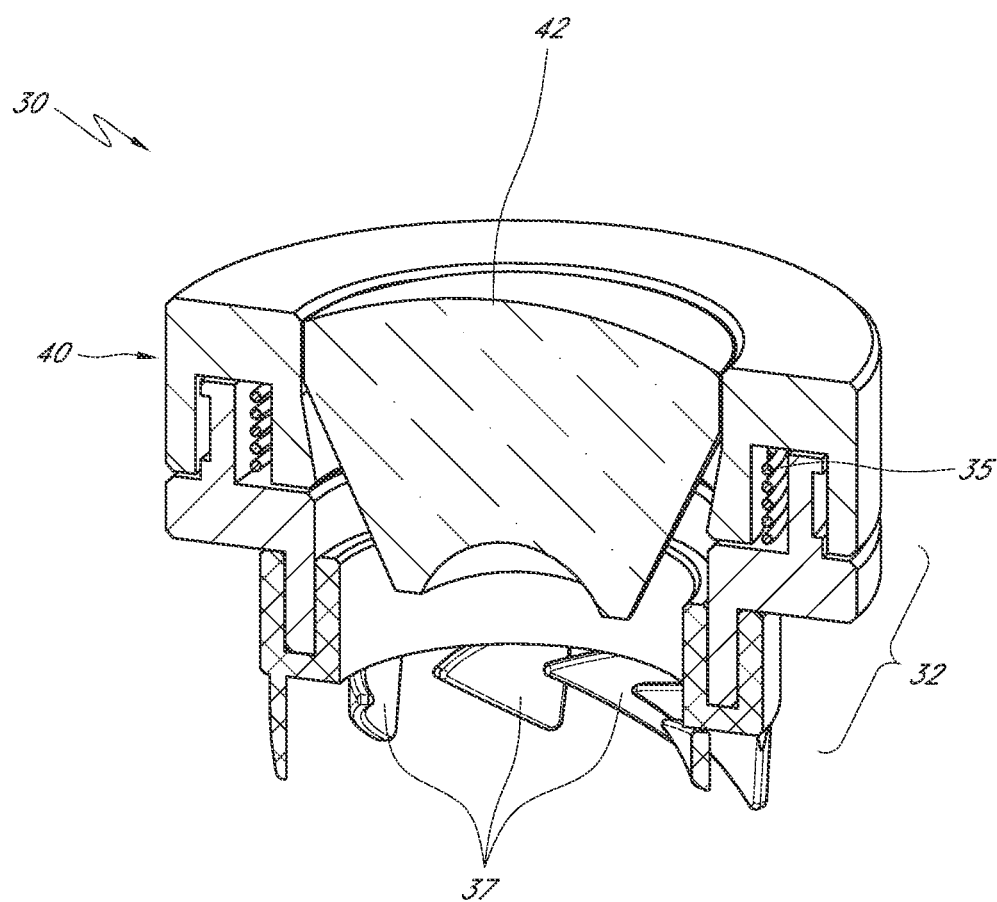

The upper (top) optical element or portion 40 may be configured to remain stationary while the lower (bottom) rotor member or portion 32 is rotated. The optical element or portion 40 includes a goniolens, gonioscope, or gonioprism or other lens or visualization member 42 that advantageously facilitates visualization (e.g., magnified visualization) of the regions of blood 28 where the rotor member 32 has generated blood reflux. The optical element or portion 40 can be held in the hand and does not rotate. The rotor member 32 may be rotated by hand (e.g., using a handle or lever, not shown) or with an internally wound spring 35 (as shown in FIG. 4I).

Compression Elements

The handheld peristaltic rotor device 30 can include a plurality of compression elements 37. In general, the plurality of compression elements 37 can be configured to apply pressure to an episcleral region of the eye, thereby occluding one or more episcleral veins to produce blood reflux within Schlemm's canal 22. The plurality of compression elements 37 can include two or more concentric spiral protrusions on a distal rim surface 39 of the rotor member 32, as best shown in FIGS. 4B, 4D, and 6B. The compression elements 37 may comprise ribs or fins.

The embodiments of the rotor members 32 shown in FIGS. 4E-4I show alternative embodiments of shapes and configurations of the compression elements 37. The compression elements 37 may include a plurality of compliant compression ribs or fins that are configured to spin below the limbus region of the eye to peristaltically force blood into Schlemm's canal. The number and size of the ribs may vary (e.g., 6 ribs, 7 ribs, 8 ribs, 9 ribs, 10 ribs, 11 ribs, 12 ribs).

The plurality of compression elements 37 can be a plurality of linear protrusions having a curved surface, each protrusion having a thickness and a maximum height configured to substantially occlude one or more episcleral veins and produce blood reflux within Schlemm's canal 22. For example, the thickness and the height of a compression element can be about 0.4 mm to about 7 mm (e.g., between 0.4 mm and 1.5 mm, between 0.5 mm and 2.5 mm, between 1 mm and 4 mm, between 2 mm and 6 mm, between 3 mm and 7 mm, overlapping ranges thereof, or any value within the recited ranges). The plurality of compression elements 37 can be formed of any suitable biocompatible material. In some embodiments, the plurality of compression elements 37 can be protrusions having a flat surface or a ridged surface instead of having a curved surface. In some embodiments, the plurality of compression elements 37 can be a ring-shaped protrusion, the ring shape located concentrically with the distal rim surface 39 of the rotor member 32. In another embodiment, the plurality of compression elements 37 can be a plurality of spoke-shaped protrusions extending outward from the center of the rotor member 32. The lower (e.g., contact) surface of the compression elements 37 may be tapered such that a height of the compression element 37 varies from one end to the other (as shown, for example, in FIGS. 4E-4I). The taper profile and positioning of the compression elements 37 may be configured such that there is a continuous overlap of contact between the compression elements 37 and the eye tissue as the rotor member 32 is rotated so as to induce the peristaltic action. After a maximum height portion of a first compression element compresses an episcleral vein, the height tapers to allow the vessel to refill with blood (as compression is reduced due to the tapered profile as rotation continues). Then the maximum height portion of the next successive compression element (due to continued rotation) compresses the episcleral vein again to cause the refilled blood in the episcleral vein to be expelled into Schlemm's canal. This peristaltic mechanism continually repeats as the rotor member 32 is rotated.

In some embodiments, a user (e.g., ophthalmologist or other clinician) can place the rotor member 32 on the episcleral surface of the eye, and then manually rotate the rotor member 32 (e.g., using a handle or lever). The user may rotate the rotor member 32 to a degree that can cause the plurality of compression elements 37 to create a peristaltic movement of blood within episcleral veins, thereby inducing blood reflux within Schlemm's canal 22. In some embodiments, a user may tilt, press, or squeeze the rotor 32 and/or the handle 38 to cause the movement of blood. In some embodiments, the rotor member 32 is rotated (manually or by an internal wound spring) multiple turns or a partial turn (e.g., ¼ turn, ½ turn, ¾ turn). In some embodiments, the rotor member 32 may be rotated automatically with an internally wound spring 35 (as shown, for example, in FIG. 4I). The spring 35 may be positioned within a channel between a portion of the optical element or portion 40 and a component of the rotor member 32. One end of the spring 35 may be coupled to a rotatable component of the rotor member 32 and the other end of the spring may be coupled to the optical element or portion 40. For example, the device 30 can be provided with the spring 35 in an unwound configuration. The clinician can then rotate the rotor member 32 (e.g., in a clockwise manner) to wind up the spring 35 (either before or after placement on the eye) and then release the rotor member 32 to cause the rotor member 32 to rotate (e.g., in a counter-clockwise manner) while the optical element or portion 40 remains stationary. In some embodiments, a high-viscosity lubricant is applied between the components to act as a dampening mechanism to cause the spring 35 to unwind more slowly to facilitate the peristaltic action to generate blood reflux.

Delivery Instrument

In some embodiments, the delivery instrument can be sufficiently long to advance the implant transocularly from the insertion site across the anterior chamber to the implantation site. At least a portion of the instrument can be flexible. Alternatively, the instrument can be rigid. The delivery instrument can comprise a plurality of members longitudinally movable relative to each other. In some embodiments, at least a portion of the delivery instrument is curved or angled. In some embodiments, a portion of the delivery instrument is rigid and another portion of the instrument is flexible.

In some embodiments, the delivery instrument has a distal curvature. The distal curvature of the delivery instrument may be characterized as a radius of approximately 10 to 30 mm, and preferably about 20 mm.

In some embodiments, the delivery instrument has a distal angle. The distal angle may be characterized as approximately 90 to 170 degrees relative to an axis of the proximal segment of the delivery instrument, and preferably about 145 degrees. The angle can incorporate a small radius of curvature at the "elbow" so as to make a smooth transition from the proximal segment of the delivery instrument to the distal segment. The length of the distal segment may be approximately 0.5 to 7 mm, and preferably about 2 to 3 mm.

In some embodiments, the instruments have a sharpened forward end and are self-trephinating, e.g., self-penetrating, so as to pass through tissue without preforming an incision, hole or aperture. Alternatively, a trocar, scalpel, or similar instrument can be used to pre-form an incision in the eye tissue before passing the implant into such tissue.

For delivery of some embodiments of the ocular implant, the instrument can have a sufficiently small cross section such that the insertion site self-seals without suturing upon withdrawal of the instrument from the eye. An outer diameter of the delivery instrument preferably is no greater than about 18 gauge and is not smaller than about 27 gauge.

For delivery of some embodiments of the ocular implant, the incision in the corneal tissue is preferable made with a hollow needle through which the implant is passed. The needle has a small diameter size (e.g., 18 or 19 or 20 or 21 or 22 or 23 or 24 or 25 or 26 or 27 gauge) so that the incision is self-sealing and the implantation occurs in a closed chamber with or without viscoelastic. A self-sealing incision also can be formed using a conventional "tunneling" procedure in which a spatula-shaped scalpel is used to create a generally inverted V-shaped incision through the cornea. In a preferred mode, the instrument used to form the incision through the cornea remains in place (that is, extends through the corneal incision) during the procedure and is not removed until after implantation. Such incision-forming instrument either can be used to carry the ocular implant or can cooperate with a delivery instrument to allow implantation through the same incision without withdrawing the incision-forming instrument. Of course, in other modes, various surgical instruments can be passed through one or more corneal incisions multiple times.

Once into the anterior chamber, a delivery instrument can be advanced from the insertion site transocularly into the anterior chamber angle and positioned at a location near the scleral spur. Using the scleral spur as a reference point, the delivery instrument can be advanced further in a generally posterior direction to drive the implant into eye tissue at a location just inward of the scleral spur toward the iris. The placement and implantation of the implant can be performed using a gonioscope or other conventional imaging equipment. The delivery instrument preferably is used to force the implant into a desired position by application of a continual implantation force, by tapping the implant into place using a distal portion of the delivery instrument, or by a combination of these methods. Once the implant is in the desired position, it may be further seated by tapping using a distal portion of the delivery instrument.

The delivery instrument can include an open distal end with a lumen extending therethrough. Positioned within the lumen is preferably a pusher tube that is axially movable within the lumen. The pusher tube can be any device suitable for pushing or manipulating the implant in relation to the delivery instrument, such as, for example, but without limitation a screw, a rod, a stored energy device such as a spring. A wall of the delivery instrument preferably extends beyond pusher tube to accommodate placement within the lumen of an implant. The implant can be secured in position. For example, the implant can be secured by viscoelastic or mechanical interlock with the pusher tube or wall. When the implant is brought into position adjacent the tissue in the anterior chamber angle, the pusher tube is advanced axially toward the open distal end of the delivery instrument. As the pusher tube is advanced, the implant is also advanced. When the implant is advanced through the tissue and such that it is no longer in the lumen of the delivery instrument, the delivery instrument is retracted, leaving the implant in the eye tissue.

Some embodiments can include a spring-loaded or stored-energy pusher system. The spring-loaded pusher preferably includes a button operably connected to a hinged rod device. The rod of the hinged rod device engages a depression in the surface of the pusher, keeping the spring of the pusher in a compressed conformation. When the user pushes the button, the rod is disengaged from the depression, thereby allowing the spring to decompress, thereby advancing the pusher forward.

In some embodiments, an over-the wire system is used to deliver the implant. The implant can be delivered over a wire. Preferably, the wire is self-trephinating. The wire can function as a trocar. The wire can be superelastic, flexible, or relatively inflexible with respect to the implant. The wire can be pre-formed to have a certain shape. The wire can be curved. The wire can have shape memory, or be elastic. In some embodiments, the wire is a pull wire. The wire can be a steerable catheter.

In some embodiments, the wire is positioned within a lumen in the implant. The wire can be axially movable within the lumen. The lumen may or may not include valves or other flow regulatory devices.

In some embodiments, the delivery instrument comprises is a trocar. The trocar may be angled or curved. The trocar can be rigid, semi-rigid or flexible. In embodiments where the trocar is stiff, the implant can be, but need not be relatively flexible. The diameter of the trocar can be about 0.001 inches to about 0.01 inches. In some embodiments, the diameter of the trocar is 0.001, 0.002, 0.004, 0.005, 0.006, 0.007, 0.008, 0.009, or 0.01 inches.

In some embodiments, delivery of the implant is achieved by applying a driving force at or near the distal end of the implant. The driving force can be a pulling or a pushing applied generally to the end of the implant.

The instrument can include a seal to prevent aqueous humor from passing through the delivery instrument and/or between the members of the instrument when the instrument is in the eye. The seal can also aid in preventing backflow of aqueous humor through the instrument and out the eye. Suitable seals for inhibiting leakage include, for example, an O-ring, a coating, a hydrophilic agent, a hydrophobic agent, and combinations thereof. The coating can be, for example, a silicone coat such as MDX™ silicone fluid. In some embodiments, the instrument is coated with the coating and a hydrophilic or hydrophobic agent. In some embodiments, one region of the instrument is coated with the coating plus the hydrophilic agent, and another region of the instrument is coated with the coating plus the hydrophobic agent. The delivery instrument can additionally comprise a seal between various members comprising the instrument. The seal can comprise a hydrophobic or hydrophilic coating between slip-fit surfaces of the members of the instrument. The seal can be disposed proximate of the drainage implant when carried by the delivery instrument. Preferably, the seal is present on at least a section of each of two devices that are machined to fit closely with one another.

In some embodiments, the delivery instrument can include a distal end having a beveled shape. The delivery instrument can include a distal end having a spatula shape. The beveled or spatula shape can have a sharpened edge. The beveled or spatula shape can include a recess to contain the implant. The recess can include a pusher or other suitable means to push out or eject the implant.

The delivery instrument further can be configured to deliver multiple implants. In some embodiments, when multiple implants are delivered, the implants can be arranged in tandem.

Method of Use

Visualization

Figure 5:
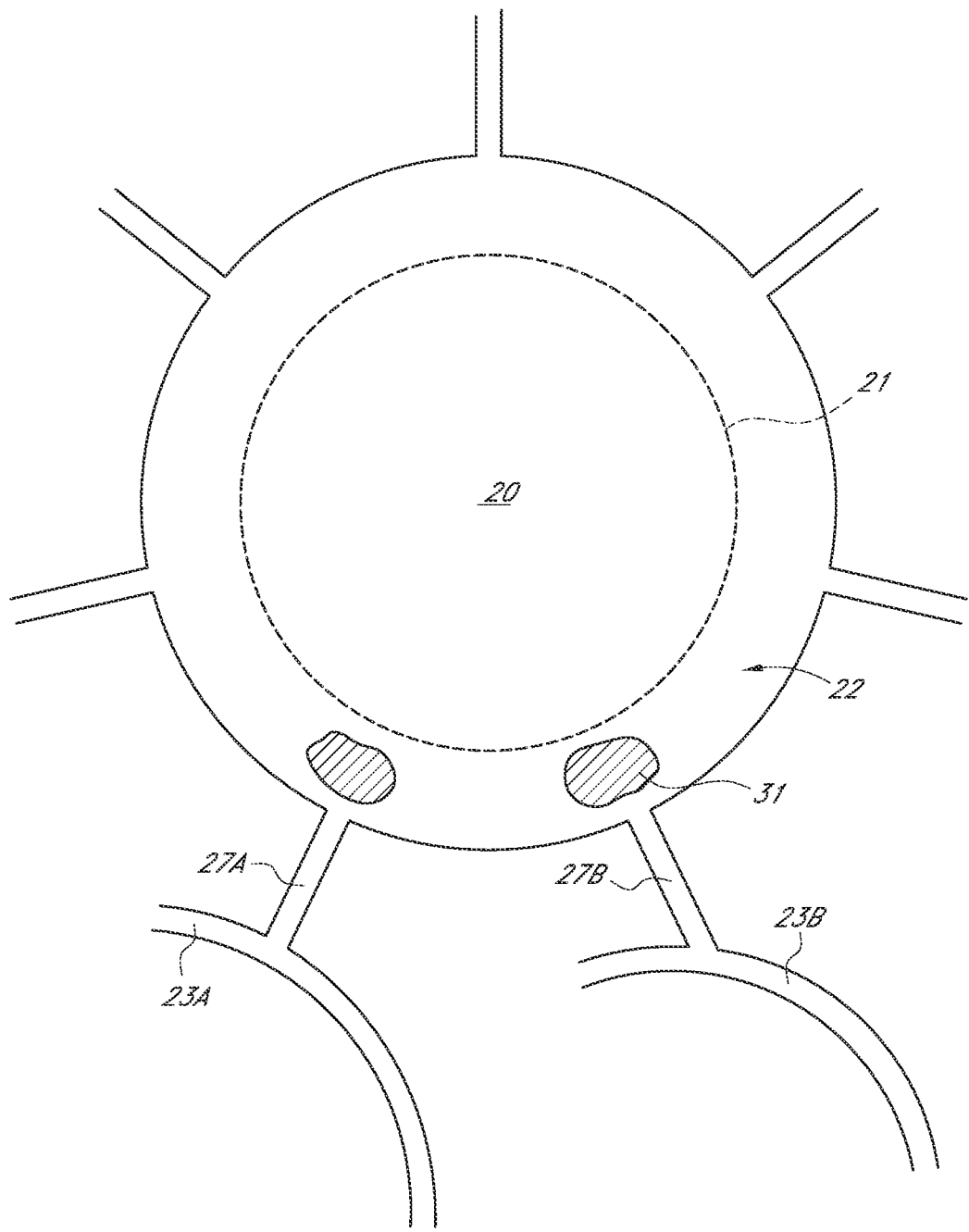
FIG. 5 illustrates a diagram illustrating blood reflux within Schlemm's canal generated by the devices of FIGS. 4A-4I.

FIG. 5 illustrates a schematic representation of a method of operation of the blood reflux-producing peristaltic rotor device 30. The rotor member 32 can be rotated (manually or by releasing an internal wound spring 35) to cause peristaltic movement of the blood to reflux into Schlemm's canal 22 (as described above). The plurality of compression elements 37 applies sufficient pressure so as to occlude the episcleral veins 23A, 23B. The location of the collector ducts 27A, 27B can be identified (e.g., using the goniolens 42) by the presence of a pinkish region 31 caused by the elevated concentration of blood within the aqueous proximal the inlets of the collector ducts 27A, 27B as compared to the remainder of the sclera. The identified locations of the collector ducts 27A, 27B can then be used to deliver one or more implants within or near the collector ducts 27A, 27B so as to enhance aqueous fluid drainage and thereby reduce intraocular pressure. The identified locations may help show the location of an outflow pathway, including the greatest outflow pathway, to which the surgeon can place the implant to maximize outflow. The identified locations of the collector ducts 27A, 27B can also be used to visualize the efficacy of the implant placed within or near the collector ducts 27A, 27B or for the retrospective placement investigation of the implant. The blood reflux-producing peristaltic rotor device 30 can be used to purge outflow pathways of obstruction.

In some embodiments, a therapeutic agent can be administered to a patient at a location proximal the identified collector duct, or collector channel, locations. The therapeutic agent can include, but is not limited to, pharmaceutical agents, biological agents including hormones, enzyme or antibody-related components, oligonucleotides, DNA/RNA vectors and live cells configured to produce one or more biological components. The therapeutic agent can be configured to cause a reduction in the intraocular pressure of the eye.

In some embodiments, the implant may comprise a surface coated by a material selected from Teflon, polyimide, hydrogel, heparin, hydrophilic compound, anti-angiogenic factor, anti-proliferative factor, therapeutic drugs, and the like. Suitable anti-angiogenic or anti-proliferative factors may be selected from, for example, protamine, heparin, steroids, anti-invasive factor, retinoic acids and derivatives thereof, and paclitaxel or its analogues or derivatives thereof.

Implantation

Figure 6A:
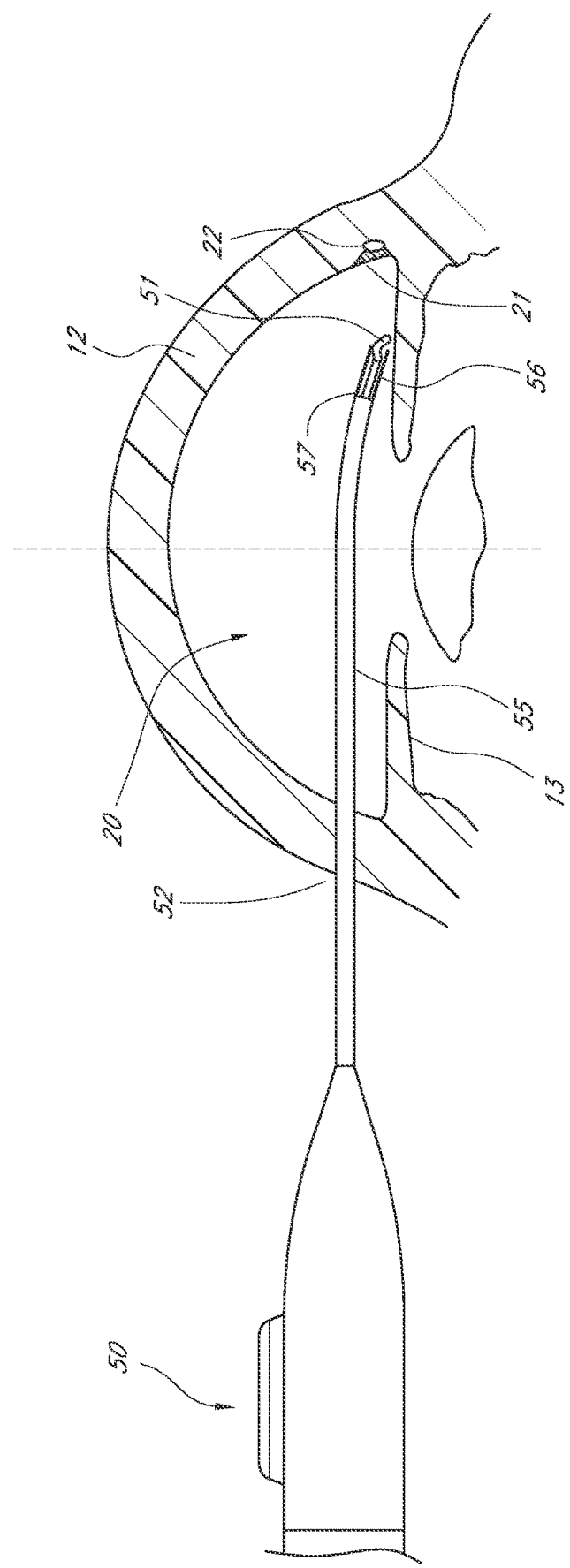
FIG. 6A illustrates an embodiment of a method for delivering implants at or near a collector duct, or channel, identified by the blood reflux produced in Schlemm's canal.
Figure 6B:
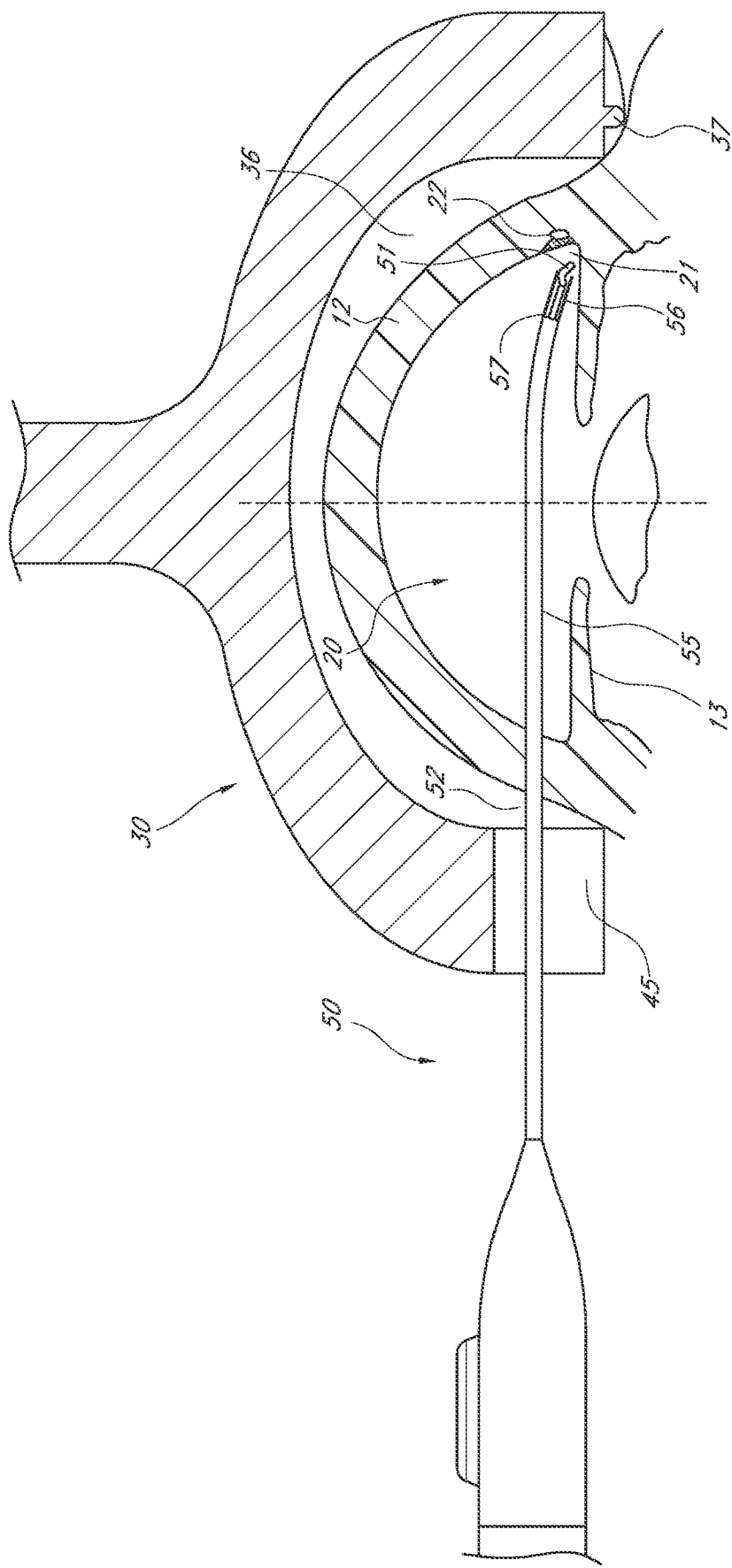
FIG. 6B illustrates the method of FIG. 6A using a peristaltic rotor device.

FIG. 6 illustrates an embodiment of a method for delivering implants at or near a collector duct identified by the blood reflux produced in Schlemm's canal. The distal rim surface 39 of the rotor member 32 of the handheld peristaltic rotor device 30 can be placed over the surface subject's eye such that the plurality of compression elements 37 occludes one or more episcleral veins, thereby allowing an ophthalmologist or other practitioner to access the temporal side of the eye through the undercut 45 of the rotor member 32. For example, the ophthalmologist can form an incision, including a small, self-sealing (e.g., less than 1 mm) incision in the cornea 12 on the temporal side of the eye, insert a delivery instrument 50 carrying an implant 51 into the incision, advance the delivery instrument across the anterior chamber and deliver the implant 51 near an identified collector duct.

In other embodiments, the peristaltic rotor device 30 can be oriented such that the plurality of compression elements 37 occludes one or more episcleral veins on a temporal side of the eye and the implant 51 can be delivered to the temporal side of the eye via an incision. In some embodiments, the delivery instrument 50 can be configured to carry multiple implants and to deliver the implants at various locations within the eye without removing the delivery instrument 50.

The delivery instrument 50 can comprise any suitable instrument for delivery of intraocular implants within the eye, such as the delivery instruments described in U.S. Patent Publication No. 2008/0228127, U.S. Patent Publication No. 2013/0253528, or U.S. patent application Ser. No. 16/132,252, the entire content of each of which is hereby expressly incorporated by reference herein. For example, the delivery instrument can comprise a cannula portion 55. The distal section of the cannula portion 55 can include a distal space 56 for holding an implant 51. The proximal end 57 of the lumen of the distal space 56 can be sealed from the remaining lumen of the cannula portion 55. In some embodiments, the delivery instrument 50 can comprise a microknife, a pointed guidewire, a sharpened applicator, a screw shaped applicator, an irrigating applicator, or a barbed applicator. In other embodiments, the incision can be formed by a blade, scalpel, or other suitable instrument or by retrograde fiberoptic laser ablation and the delivery instrument 50 can then be inserted through the preformed incision.

Figure 7:
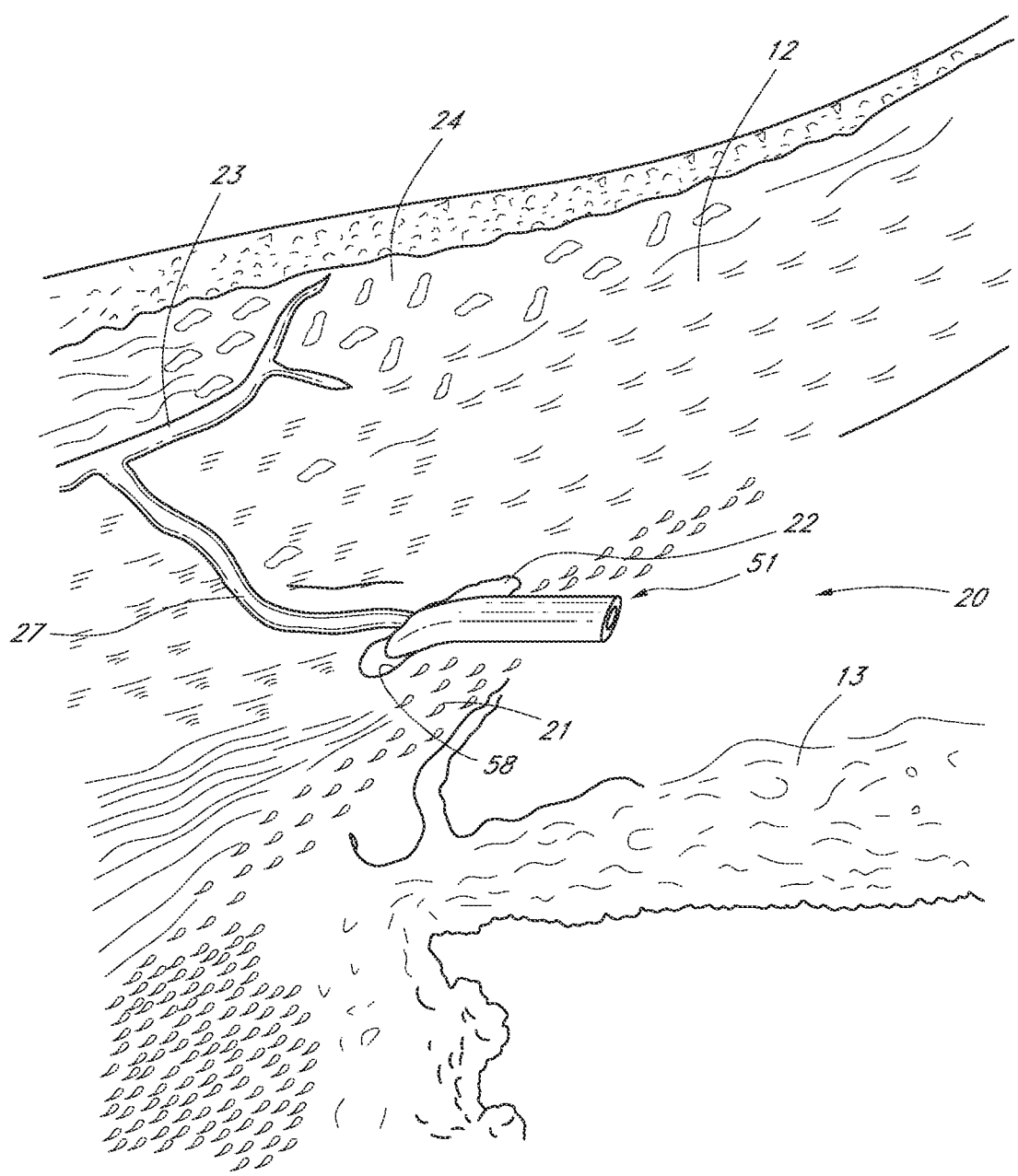
FIG. 7 illustrates placement of an implant at or near a location (e.g., an identified location based on blood reflux) of a collector duct, or channel, of Schlemm's canal of the eye.

FIG. 7 illustrates a perspective view of the anterior chamber angle of an eye 10 with the implant 51 having been positioned near an identified collector duct 27 within Schlemm's canal 22. The inlet end of the implant 51 is exposed to the anterior chamber 20 while the outlet end is positioned within an inner wall 58 of Schlemm's canal 22 near the collector duct 27. In some embodiments, the outlet end of the implant is positioned within 1 mm of the identified location of the collector duct 27. In a further embodiment, the outlet end may be positioned within the collector duct 27. The implant 51 can be positioned to maintain a fluid passageway from the anterior chamber 20 to a location near the collector duct 27.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers or an amount that is within less than or equal to 10% of the stated amount. For example, "about 10 mm" includes "10 mm." Terms or phrases preceded by a term such as "substantially" or "generally" include the recited term or phrase. For example, "substantially transparent" includes "transparent." The terms "comprising," "including,", "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the inventions have been discussed in the context of certain embodiments and examples, it should be appreciated that the inventions extend beyond the specifically disclosed embodiments to other alternative embodiments and/or uses of the inventions and obvious modifications and equivalents thereof. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Additionally, the skilled artisan will recognize that any of the above-described methods can be carried out using any appropriate apparatus. Further, the disclosure herein of any particular feature, aspect, method, property, characteristic, quality, attribute, element, or the like in connection with various embodiments can be used in all other embodiments set forth herein. The headings used herein are merely provided to enhance readability and are not intended to limit the scope of the embodiments disclosed in a particular section to the features or elements disclosed in that section.

For purposes of this disclosure, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

What is claimed is:

1. A method of positioning intraocular implants at or near collector ducts of Schlemm's canal of an eye, the method comprising:
   positioning a handheld peristaltic rotor device on a corneal surface of an eye, the handheld peristaltic rotor device comprising a rotor having a plurality of compression elements;
   rotating the rotor such that the plurality of compression elements create a peristaltic movement of blood from one or more occluded episcleral veins to Schlemm's canal,
   identifying a location of at least one collector duct of the eye based on the refluxed blood within Schlemm's canal;
   delivering an implant through an incision in the eye; and
   placing an implant within the eye such that the implant is located at or near the identified location of the at least one collector duct.

2. The method of claim 1, wherein placing the implant within the eye comprises positioning an inlet end of the implant in an anterior chamber of the eye and positioning an outlet end of the implant proximal to the identified location of the collector duct.

3. The method of claim 2, wherein positioning the outlet end of the implant proximal to the identified location of the collector duct comprises positioning the outlet end within 1 mm of the identified location.

4. The method of claim 1, further comprising placing a second implant within the eye such that the second implant is located at or near the identified location of a second collector duct.

5. The method of claim 1, further comprising maintaining a fluid passageway from the anterior chamber to the collector duct through the implant.

6. The method of claim 1, further comprising delivering a therapeutic agent to the at least one collector duct.

7. A method of identifying a location of one or more collector ducts of Schlemm's canal of an eye, the method comprising:
   positioning a handheld peristaltic rotor device on a surface of an eye, the handheld rotor device comprising a rotor having a compression element;
   rotating the rotor such that the compression element of the rotor induces a peristaltic movement of blood into Schlemm's canal from one or more occluded episcleral veins, and
   identifying a location of at least one collector duct of the eye based at least in part on the refluxed blood.

8. The method of claim 7, further comprising administering a drug to the identified location of the collector duct.

9. The method of claim 7, wherein rotating the rotor comprises manual rotation.

10. The method of claim 7, wherein rotating the rotor comprises winding a spring by manually rotating the rotor in a clockwise direction and then releasing the rotor to cause the spring to unwind and the rotor to rotate in a counter-clockwise direction.

* * * * *

UNITED STATES PATENT AND TRADEMARK OFFICE
CERTIFICATE OF CORRECTION

PATENT NO. : 12,226,308 B2
APPLICATION NO. : 17/444960
DATED : February 18, 2025
INVENTOR(S) : Charles Raymond Kalina, Jr.

It is certified that error appears in the above-identified patent and that said Letters Patent is hereby corrected as shown below:

On the Title Page

Under item (56), Other Publications:

Column 2, Line 1, delete "al., Disistronic Polloviruses as" and insert -- al., Dicistronic Polioviruses as --.

Under item (56), U.S. Patent Documents:

Column 1, page 4, Line 11, delete "Dom et al." and insert -- Dorn et al. --.

Column 2, page 4, Line 49, delete "Grimaldi et al." and insert -- Crimaldi et al. --.

Column 1, page 6, Line 54, delete "Karageoziar" and insert -- Karageozian --.

Signed and Sealed this
Twenty-seventh Day of May, 2025

Coke Morgan Stewart
*Acting Director of the United States Patent and Trademark Office*